US012746069B2

(12) United States Patent
Polchin

(10) Patent No.: US 12,746,069 B2
(45) **Date of Patent: *Sep. 29, 2026**

(54) AUTO-NAVIGATING DIGITAL SURGICAL MICROSCOPE

(71) Applicant: Aesculap AG, Tuttlingen (DE)

(72) Inventor: George C. Polchin, Santa Barbara, CA (US)

(73) Assignee: Aesculap AG, Tuttlingen (DE)

( * ) Notice: Subject to any disclaimer, the term of this patent is extended or adjusted under 35 U.S.C. 154(b) by 378 days.

This patent is subject to a terminal disclaimer.

(21) Appl. No.: 18/029,551

(22) PCT Filed: Oct. 1, 2021

(86) PCT No.: PCT/US2021/053181
§ 371 (c)(1),
(2) Date: Mar. 30, 2023

(87) PCT Pub. No.: WO2022/072835
PCT Pub. Date: Apr. 7, 2022

(65) Prior Publication Data

US 2023/0363830 A1 Nov. 16, 2023

Related U.S. Application Data

(60) Provisional application No. 63/243,659, filed on Sep. 13, 2021, provisional application No. 63/086,310, filed on Oct. 1, 2020.

(51) Int. Cl.
*A61B 34/20* (2016.01)
*A61B 90/00* (2016.01)
(Continued)

(52) U.S. Cl.
CPC .............. *A61B 34/20* (2016.02); *A61B 90/25* (2016.02); *A61B 90/37* (2016.02);
(Continued)

(58) Field of Classification Search
CPC ......... A61B 34/20; A61B 90/25; A61B 90/37; A61B 2034/2057; A61B 2090/371;
(Continued)

(56) References Cited

U.S. PATENT DOCUMENTS

| | | | |
|---|---|---|---|
| 2001/0034530 A1 | 10/2001 | Malackowski et al. | |
| 2012/0143049 A1 | 6/2012 | Neubauer et al. | |

(Continued)

FOREIGN PATENT DOCUMENTS

| | | | |
|---|---|---|---|
| WO | 2006095027 | A1 | 9/2006 |
| WO | 2022/072835 | A1 | 4/2022 |
| WO | 2023/039596 | A1 | 3/2023 |

OTHER PUBLICATIONS

International Search Report and Written Opinion mailed Jan. 10, 2022 for International Application Serial No. PCT/US2021/053181 filed on Oct. 1, 2021.

(Continued)

*Primary Examiner* — Eugene T Wu
(74) *Attorney, Agent, or Firm* — K&L Gates LLP

(57) ABSTRACT

New and innovative systems and methods for auto-navigation in an integrated surgical navigation and visualization system are disclosed. An example system comprises: a single cart providing motility; a stereoscopic digital surgical microscope comprising a surgical visualization camera and a localizer; one or more computing devices (e.g., a single computing device powered by a single power connection) housing and jointly executing a surgical navigation module and a surgical visualization module, wherein the localizer is associated with the surgical navigation module, and wherein the surgical visualization camera is associated with the surgical visualization module; a single unified display; a processor; and memory. The system may generate a transformation of patient data associated with a patient to the surgical visualization camera; calibrate the surgical visual- (Continued)

800 ization camera and the localizer; provide visualization of the surgical site via the single unified display; and provide navigation of the surgical site responsive to user input.

20 Claims, 16 Drawing Sheets

(51) Int. Cl.
*A61B 90/25* (2016.01)
*G02B 21/00* (2006.01)
*G02B 21/22* (2006.01)

(52) U.S. Cl.
CPC ......... *G02B 21/0012* (2013.01); *G02B 21/22* (2013.01); *A61B 2034/2057* (2016.02); *A61B 2090/371* (2016.02)

(58) Field of Classification Search
CPC ..... A61B 5/0086; A61B 5/066; A61B 5/4064; A61B 5/4887; A61B 5/7425; A61B 2017/00203; A61B 2017/00725; A61B 2034/107; A61B 2034/2065; A61B 2034/207; A61B 2090/365; A61B 90/20; A61B 6/032; A61B 6/5229; A61B 2034/2055; A61B 2576/026; A61B 6/12; G02B 21/0012; G02B 21/22; G02B 21/365
See application file for complete search history.

(56) References Cited

U.S. PATENT DOCUMENTS

| | | | |
|---|---|---|---|
| 2014/0350961 A1 | 11/2014 | Csurka et al. | |
| 2015/0164329 A1 | 6/2015 | Schmidt et al. | |
| 2015/0300816 A1 | 10/2015 | Yang et al. | |
| 2016/0048953 A1 | 2/2016 | Zhao et al. | |
| 2017/0251990 A1 | 9/2017 | Kheradpir et al. | |
| 2017/0281297 A1 | 10/2017 | Tuma et al. | |
| 2018/0303574 A1* | 10/2018 | Ramirez Luna ..... | H04N 13/257 |
| 2018/0353059 A1* | 12/2018 | Tesar ..................... | A61B 90/30 |
| 2020/0281667 A1 | 9/2020 | Blondel et al. | |
| 2024/0390075 A1 | 11/2024 | Minne et al. | |

OTHER PUBLICATIONS

International Search Report and Written Opinion mailed Dec. 15, 2022 for International Application Serial No. PCT/US2022/076349 filed on Sep. 13, 2022.
Suenaga et al., "Vision-based markerless registration using stereo vision and an augmented reality surgical navigation system: a pilot study", BMC medical imaging, Nov. 2, 2015, 15.1 (2015): pp. 1.11.

* cited by examiner

AUTO-NAVIGATING DIGITAL SURGICAL MICROSCOPE

RELATED APPLICATIONS

This present application is a national phase filing of International Application No. PCT/US2021/053181, filed on Oct. 1, 2021, which claims the benefit of U.S. Provisional Application No. 63/086,310, filed on Oct. 1, 2020, and entitled "AUTO-NAVIGATING DIGITAL SURGICAL MICROSCOPE," the disclosure of which is hereby incorporated by reference in its entirety. This present application also claims the benefit of U.S. Provisional Application No. 63/243,659, filed on Sep. 13, 2021, and entitled "INTEGRATED SURGICAL NAVIGATION AND VISUALIZATION SYSTEM, AND METHODS THEREOF," the disclosure of which is hereby incorporated by reference in its entirety.

TECHNICAL FIELD

Certain aspects of the present disclosure generally relate to surgical systems, and specifically relate to systems and methods for auto-navigation of an integrated surgical navigation and visualization.

BACKGROUND

Surgical navigation can better patient outcomes by guiding the surgeon toward and through the target surgical site using volumetric patient data from computed tomography (CT), magnetic resonance imaging (MRI) and diffusion tensor imaging (DTI) modalities. The surgical navigation system can register the physical patient to the volumetric patient data, allowing display of the current location in the patient data of a given surgical tool such as a navigated pointer while said tool is located on or in the live patient.

Various navigation devices exist currently in industry. In an example conventional design, a navigation device projects a pattern of near infrared light (NIR) pulses to the scene typically synchronized to the frame exposure of the stereoscopic navigation camera. The NIR light is reflected back by a multitude of retroreflectors mounted at known places in an imaginary reference frame, or, alternatively, the NIR LEDs are used in the targets, synchronized to the navigation camera frame exposure via hard wire, or by using a photodetector to "see" the flash from the localizer and trigger the immediate emission of the NIR LEDs.

Surgical visualization with a surgical microscope can be used in many surgeries, such as neurological, orthopedic and reconstructive surgeries, where visualization of small structures is needed. Surgical visualization systems may include cameras provided by digital surgical microscopes. However, there is a desire to more closely integrate surgical visualization systems with surgical navigation systems, including a desire to more closely align visualization and navigation devices.

Surgical navigation systems today (e.g., MEDTRONIC's STEALTH and BRAINLAB's CURVE) are often separate and discrete from surgical visualization systems (e.g., ZEISS'S KINEVO and LEICA's OH SERIES). Any integration between the surgical navigation and surgical visualization is typically limited. For example, some systems combine the functions of navigation and visualization by including the navigation of the microscope view as a tool to show position of the microscope focal point. Some systems show the microscope field of view on the volumetric patient data, or register the volumetric patient data view onto the microscope's field of view via ocular image injection, display the resulting view in an external monitor. For example, navigation systems such as MEDTRONIC's STEALTH and BRAINLAB's CURVE, can be optionally integrated with certain microscopes (e.g., ZEISS'S KINEVO and LEICA's OH SERIES). Some manufacturers (e.g., STRYKER and SYNAPTIVE) can form commercial agreements where separate navigation and microscope systems are packaged as one product but remain as separate devices.

The discrete nature of the individual components of such paired systems (e.g., a surgical navigation system and a surgical visualization system) can lead to difficulties in setup and use. Such difficulties often lead to non-use or underutilization of such systems. Such difficulties include, but are not limited to: having too many physical pieces of equipment ("too much furniture") for operating rooms with limited space; an excess of cables needed to connect the individual components of the paired system to each other and to power; technical difficulties in connecting the individual components of the paired system communicatively and functionally; and challenges in calibrating the surgical and visualization components for a unified functionality.

Furthermore, there is a desire to provide auto-navigation capabilities in integrated surgical navigation and visualization systems.

Various embodiments of the present disclosure address one or more of the shortcomings presented above.

SUMMARY

The present disclosure provides new and innovative systems and methods for auto-navigation in an integrated surgical navigation and visualization system. The auto-navigating integrated surgical navigation and visualization system provides surgical planning, patient registration, surgical navigation, and visualization with robotic positioning, all in a single cart-based operating room appliance that takes up only 60% of precious floor space needed for existing solutions. Extending the existing digital surgical robotic microscopes (e.g., surgical visualization devices) with navigation capabilities has many advantages over legacy surgical navigation including: one-click automated patient registration; better accuracy; increased ease of use; reduced mental load for the surgeon; significantly smaller operating room footprint; reduced downtime from line-of-sight issues; and enables less invasive procedures, overall reduced patient exposure time and better patient outcomes.

In an example, an auto-navigating and integrated surgical navigation and visualization system is disclosed. The system comprises a single cart providing motility; a stereoscopic digital surgical microscope; one or more computing devices (e.g., including a single computing device) housing and jointly executing a surgical navigation module and a surgical visualization module, and powered by a single power connection, thus reducing operating room footprint; a single unified display; a processor; and memory. The system may further include a localizer (e.g., a navigation camera or device) associated with the surgical navigation module; and a surgical visualization camera affixed to the stereoscopic digital surgical microscope and associated with the surgical visualization module. Furthermore, the system may provide the basis for extension from a stereoscopic digital surgical microscope to an N-camera digital surgical microscope where N is 2 or greater.

In some aspects, the surgical navigation module (e.g., a navigation device) may be integrated into a digital surgical microscope (DSM) head of the stereoscopic digital surgical microscope. The DSM head and/or the stereoscopic digital surgical microscope may be mounted on a robotic arm. The single cart may support the robotic arm as well as the single unified display (e.g., the boom-mounted 3D stereoscopic display). Also or alternatively, the single cart may support a mast-mounted touchscreen for user input. Additional displays can also be connected optionally. The surgical navigation module (e.g., the navigation device) may provide 6 degrees of freedom (6DoF) position and orientation information of the DSM head relative to some reference or target viewable by the surgical navigation module in the scene. The remainder of the integrated surgical navigation and visualization system may provide stereoscopic visualization over a range of magnifications (e.g., 1×-9×) and a range of working distances (e.g., 200 mm-450 mm.)

An objective of surgical navigation and/or visualization may involve guiding the surgeon around the patient's anatomy during a surgical procedure so that the surgeon can complete the procedure in the most effective, least damaging way.

The patient's anatomy has typically been scanned in a device such as a computed tomography (CT) machine or a magnetic resonance imaging (MRI) machine, and the results stored in a format such as a stack of image "slices" of the anatomy from which the 3D anatomy can be reconstructed and explored.

The objective of surgical navigation may thus be achieved by providing a view or views of various levels of relative position and orientation information between the patient data and various objects such as a navigation probe and/or the digital surgical microscope's optical axis.

The memory stores computer-executable instructions that, when executed by the processor, causes the system to perform one or more steps. For example, the system may generate a transformation of patient data associated with a patient to the surgical visualization camera; calibrate the surgical visualization camera and the localizer; provide navigation of a surgical site responsive to user input; and provide visualization of the surgical site via the single unified display.

In some aspects, generating the transformation of patient data associated with the patient to the surgical visualization camera may include one or more of: generating, at a single zoom and a working distance for each camera eye associated with each of the surgical visualization camera and the localizer, a first transformation of the localizer to the surgical visualization camera (e.g., camEye_T_localizer); generating, over a range of a zoom and the working distance for each camera eye associated with each of the surgical visualization camera and the localizer, a second transformation of the localizer to the surgical visualization camera (e.g., camEye_T_localizer); performing, using the first transformation of the localizer to the surgical visualization camera and the second transformation of the localizer to the surgical visualization camera, a patient registration of the patient to determine transformation of the patient data to the target position of the patient (e.g., a pose of a relevant patient anatomy of the patient relative to the target position of the patient (e.g., patientTarget_T_patientData)); generating, using the transformation of the patient data to the target position of the patient, a transformation of the target position of the patient to the localizer (e.g., localizer_T_patientTarget); or generating, based on the transformation of the target position to the localizer, a transformation of the patient data associated with the patient to the surgical visualization camera (e.g., camEye_T_patientData).

The system may also perform a startup of the surgical navigation module and the digital surgical microscope. Furthermore, the system may synchronize, in real time, the visualization of the surgical site with the navigation of the surgical site. For example, the system may provide integrated navigation information and microscope surgical site visualization via the unified display. Also or alternatively, the system may provide navigation information overlaying the live surgical view in stereoscopic view at the same plane of focus for all views.

In at least one aspect, the system may control a position of the stereoscopic digital surgical microscope with a given reference (e.g., optical axis). For example, the given reference of the digital surgical microscope aligns quasi-continuously in quasi-real-time with a central axis of a NICO port or a spinal dilator tool. Also or alternatively, the system may receive a user input associated with a pre-planned trajectory for the navigation of the surgical site; and the system may control the position of the stereoscopic digital surgical microscope by aligning the given reference of the digital surgical microscope with the pre-planned trajectory.

In at least one embodiment, the system may provide touchless registration (e.g., of a patient) via the use of the focal point of the digital surgical microscope instead of a navigated probe for use in fiducial matching, landmark matching and trace methods of patient registration. For example, the system may prompt touchless registration of the patient; and receive user input associated with the touchless registration of the patient. The system may receive the user input associated with the touchless registration via photogrammetry or stereogrammetry.

Moreover the system may confer several advantages, including but not limited to: reducing communication latency and connectivity risk (e.g., by housing and jointly executing the surgical navigation module and the surgical visualization module in the computing system); eliminating or reducing the need to connect two systems (e.g., for navigation and visualization) such that the workflow of both work correctly and in synchronization, eliminating or reducing any workflow step(s) required to connect the two systems to each other; eliminating or reducing physical cabling or other communication connection requirement between the two systems; reducing power cable requirements compared to two discrete systems; and easing line-of-sight problems.

In an example, a method performed by a computing device having one or more processors may include: performing a startup of the computing system, causing a startup of a surgical navigation module and a surgical visualization module, wherein the surgical navigation module and the surgical visualization module are jointly housed in and executed by the computing system; generating a transformation of patient data associated with a patient at a surgical site to a surgical visualization camera associated with the surgical visualization module; calibrating the surgical visualization camera and a localizer associated with the surgical navigation module; providing navigation of the surgical site responsive to user input; and providing visualization of the surgical site via a single unified display.

The method may include. controlling a position of a stereoscopic digital surgical microscope with a given reference. The method may further include: receiving, by the computing system, a user input associated with a pre-planned trajectory for the navigation of a surgical site by a stereoscopic digital microscope; and aligning the given reference of the digital surgical microscope with the pre-planned trajectory.

In an example, a non-transitory computer-readable medium for use on a computer system is disclosed. The non-transitory computer-readable medium may contain computer-executable programming instructions may cause processors to perform one or more steps or methods described herein.

Additional features and advantages of the disclosed method and apparatus are described in, and will be apparent from, the following Detailed Description and the Figures. The features and advantages described herein are not all-inclusive and, in particular, many additional features and advantages will be apparent to one of ordinary skill in the art in view of the figures and description. Moreover, it should be noted that the language used in the specification has been principally selected, for readability and instructional purposes, and not to limit the scope of the inventive subject matter.

DETAILED DESCRIPTION

Figure 1A:
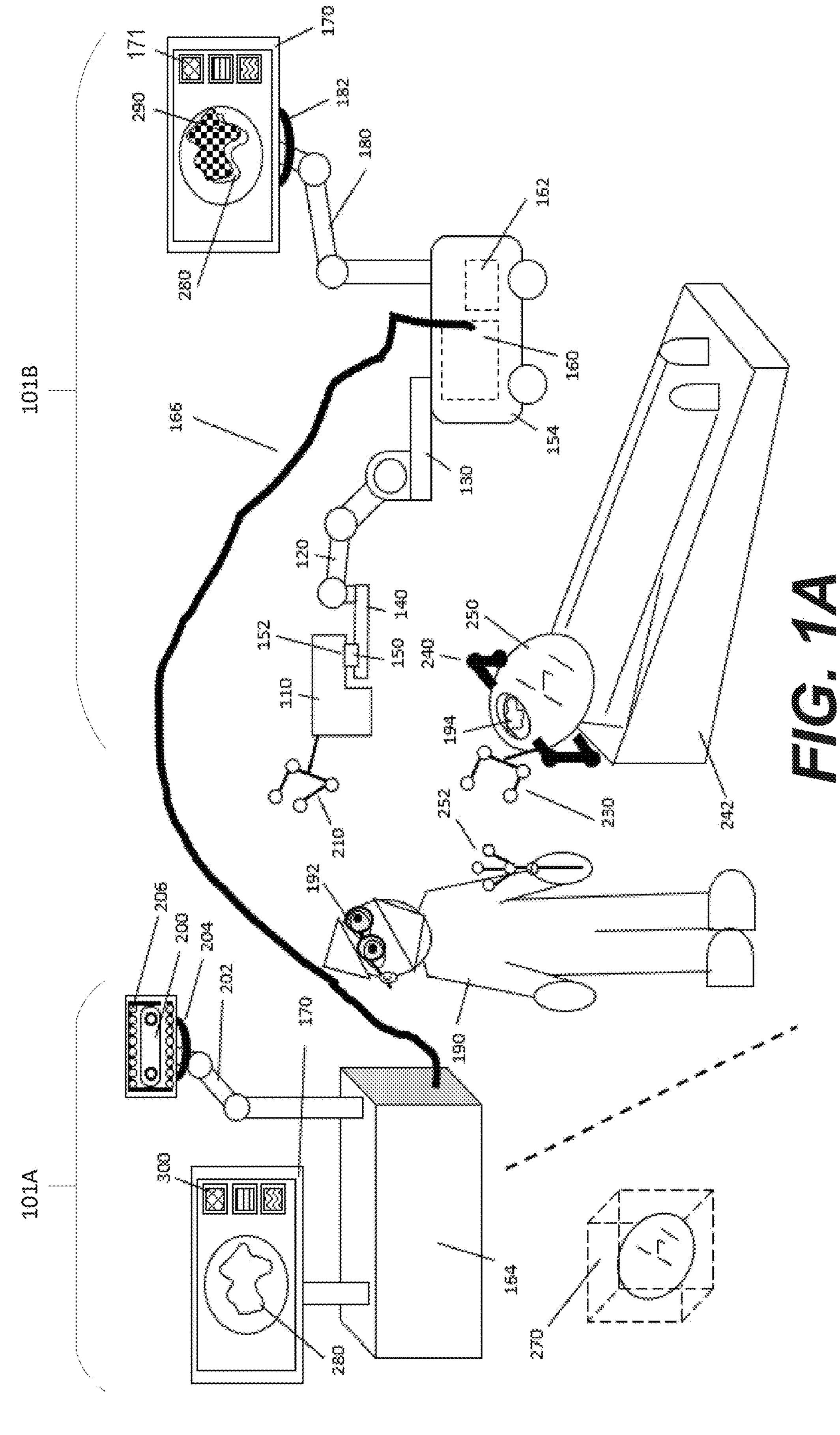
FIG. 1A is a diagram showing separate and distinct navigation and visualization systems, according to an example embodiment of the present disclosure.

The present disclosure relates in general to auto-navigation in an integrated surgical navigation and visualization system used in surgical sites. As previously discussed, there is a desire to better integrate surgical visualization systems with surgical navigation systems, such as a surgical visualization device (e.g., a digital surgical microscope camera) integrating a navigation device (e.g., a localizer). For example, a stereoscope camera mounted in the microscope head and operating in the visible spectrum viewing simple patterns in the scene (such as April tags, Aruco patterns, checkerboard/chessboard, offset circle patterns) can provide significantly better accuracy than the stereoscopic localizer. Accuracy is also improved when the stereoscopic camera is mounted with appropriate optics at the closer range afforded by integrating both the visualization and the navigation camera into the microscope head as discussed in various embodiments described herein. A monoscopic camera mounted in the microscope head and operating in the visible spectrum can provide much the same information but at reduced manufacturing cost and computational requirements compared to the stereoscopic version. Operating either such camera in the near infrared (with optics, lighting and reflectors or emitters to match) can increase performance metrics such as robustness to scene lighting at the cost of more complicated and costly equipment. Furthermore, the smaller distance between the surgical navigation camera (e.g., localizer) and the navigation targets, as well as the smaller distance and/or angle between the surgical navigation camera (e.g., localizer) and the surgical visualization camera eye may further reduce errors (e.g., relating to the synchronization between navigation and visualization). Furthermore, the placement of the microscope head, which may include both the surgical navigation (e.g., localizer) and visualization devices), closer to the patient may further reduce errors.

In some embodiments, surgical navigation systems (e.g., localizers) may be integrated into surgical visualization systems (e.g., stereoscopic digital surgical microscopes) via other devices that assist the navigation device in meeting the requirements of being able to be integrated into the digital surgical microscope (DSM) head (e.g., size, weight, and optical parameters such as working distance and field of view). These other devices may also provide 6 DoF position and orientation information relative to some reference in the scene. Examples include a depth camera, such as Intel RealSense, or structured light such as Projector (TI picoDLP) and image sensor (standard CMOS monoscopic camera).

U.S. Pat. No. 10,299,880, the entirety of which is hereby incorporated by reference herein, discloses a digital surgical robotic microscope head with navigation capabilities. The example stereoscopic visualization camera disclosed therein comprises a digital stereoscopic visualization platform with full-range, operator-independent orientation for microsurgical applications. Extending the digital surgical robotic microscope disclosed in U.S. Pat. No. 10,299,880 with navigation capabilities has many advantages over legacy surgical navigation including: one-click automated patient registration; better accuracy; increased ease of use; reduced mental load for the surgeon; significantly smaller operating room footprint; reduced downtime from line-of-sight issues;

and enables less invasive procedures, overall reduced patient exposure time and better patient outcomes.

At least one embodiment includes a single medical device providing the multiple functions of a surgical navigation device and of a versatile digital surgical microscope. The use of the single medical device helps to reduce operating room (OR) footprint. This reduction is important in most operating rooms, which are already crowded due to the many medical devices required for most surgeries.

In at least one embodiment, the integrated surgical navigation and visualization system is seamlessly rendered as ready to use. For example, the integrated system may be seamlessly powered by a single power cord. Once the integrated system has been plugged-in, and turned on, the integrated system may be ready for use. The seamless start-up procedure may eliminate: the need to connect two discrete systems with burdensome cables; the need to connect two discrete systems with problem-prone wireless communications; any workflow-related step(s) required to connect the two discrete systems to each other; the need to connect two discrete systems such that the workflow of both work correctly and in synchronization; and the risk that an upgrade to one piece of a multi-component system will break the functionality of the combined system.

In at least one embodiment, the integrated surgical navigation and visualization system may include a single and/or centralized computer system. For example, the visualization and the surgical navigation software modules may be resident within, and execute inside, the same computer, thereby reducing communication latency and connectivity risk. This arrangement may eliminate the need to position multiple pieces of equipment in an operating room which might have limited space. The tighter footprint and elimination of remote and/or separate localizer modules may ease line-of-sight problems.

In at least one embodiment, the integrated surgical navigation and visualization system may eliminate the need to add a separate navigation target to a head of a microscope (e.g., "microscope head"). As such navigation targets are typically made by manufacturers specializing in surgical navigations, and not by manufacturers specializing in surgical visualization (e.g., microscope companies), the elimination of this need helps to create a more efficient manufacture and assembly. The elimination of this need helps to reduce line-of-sight problems from the navigation camera to the microscope navigation target, helps to provide integrated navigation information and surgical site visualization on a unified display area.

Furthermore, the integrated surgical navigation and visualization system may help provide navigation information overlaying the live surgical view in stereoscopic view at the same plane of focus for all views. This arrangement may alleviate the problem of the surgeons having to refocus their eyes as they look from live surgical site to overlay.

Furthermore, the integrated surgical navigation and visualization system may eliminate interference of navigation infrared (IR) light source with fluorescence light source(s). Microscope fluorescence and navigation light may typically use same or similar light wavelengths, limiting the usability and efficacy of the fluorescence.

Furthermore, the integrated surgical navigation and visualization system may draw user-planned virtual incision and/or other approach patterns and/or paths which persist optionally under control of the user throughout the time of the surgical approach instead of being removed (and thus rendered useless) as are physical marks on the patient's skin. For example, the integrated surgical navigation and visualization system can draw user-planned virtual craniotomy plans, which may persist optionally under control of the user throughout the time of the surgical approach instead of being removed as the craniotomy proceeds. As another example, the integrated surgical navigation and visualization system may draw user-planned trajectory plans, which may persist optionally under control of the user throughout the time of the surgical approach. Such guidance may also be updateable, e.g., to correct any errors as the procedure progresses.

Furthermore, the integrated surgical navigation and visualization system may allow the user to add planned waypoints to patient data specifying desired poses of the digital surgical microscope at various points in the surgical procedure.

In addition, the integrated surgical navigation and visualization system may connect robot space to patient space. This connection provides a set of additional novel and nonobvious features including, but not limited to: an alignment the optical axis of the digital surgical microscope under user option quasi-continuously in quasi-real-time with a navigated vector positioned in space such as the central axis of a NICO port or the central axis of a spinal dilator tool; an alignment of the optical axis of the digital surgical microscope under user option with a pre-planned trajectory; and/or a continuous or substantially continuous alignment of the optical axis of the digital surgical microscope under user option with a tool or portion of tool geometry.

Furthermore, the integrated surgical navigation and visualization system may provide a basis for extending the concept of a two-camera stereoscopic digital surgical microscope to an N-camera digital surgical microscope where N is 2 or greater.

In some embodiments, the integrated surgical navigation and visualization system may comprise a navigation device integrated into the visualization device. For example, a digital surgical microscope head may comprise both the navigation device and the visualization device.

In further embodiments, the integrated surgical navigation and visualization system may provide automatic navigation for the digital surgical microscope. The automatic navigation may be facilitated by a transformation of patient data associated with a patient to the visualization camera affixed to the digital surgical microscope.

I. Surgical Environment

Figure 1B:
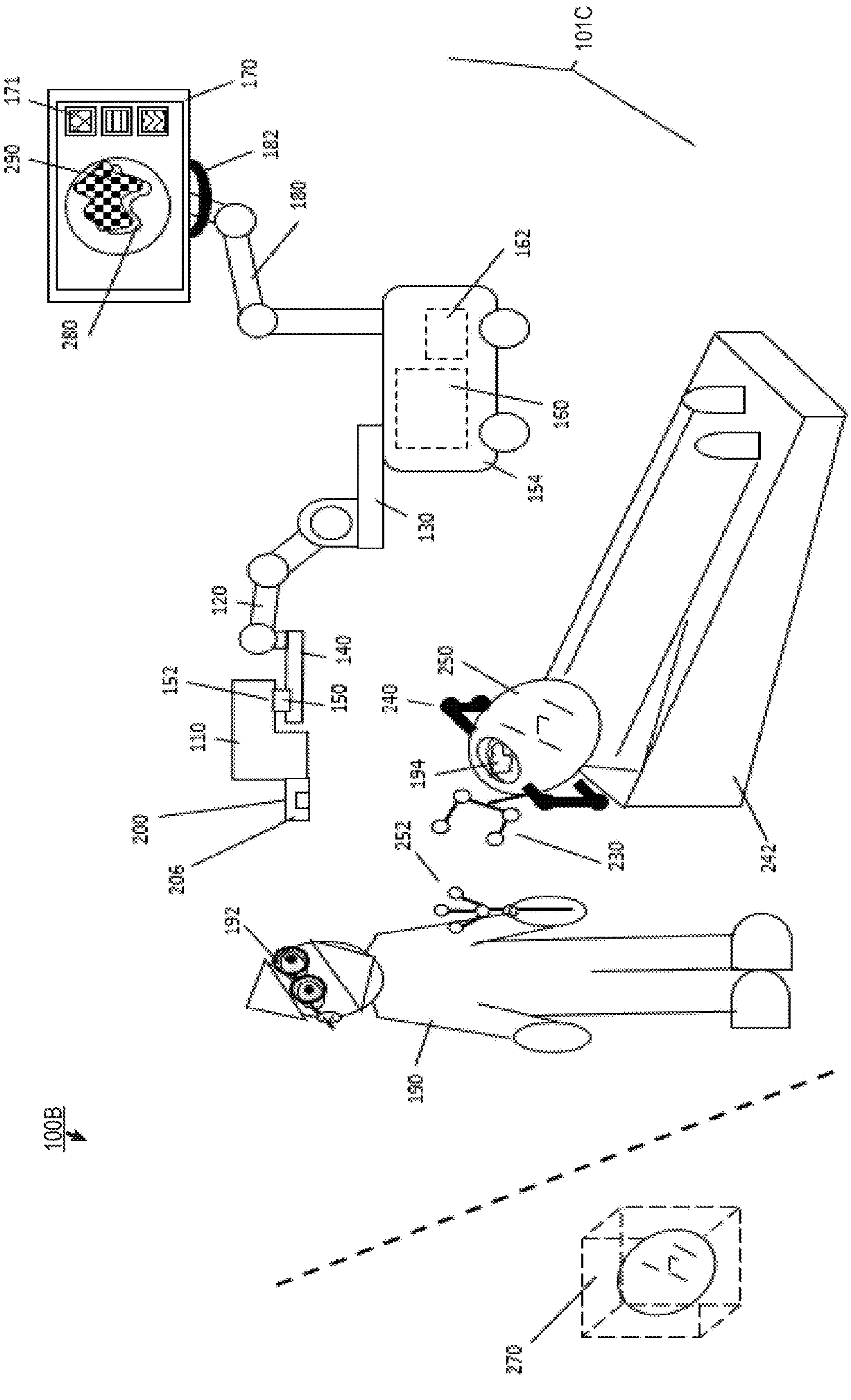
FIG. 1B is a diagram showing an example surgical environment of the integrated surgical navigation and visualization system with auto-navigation, according to an example embodiment of the present disclosure.

FIG. 1A is a diagram showing separate and distinct navigation and visualization systems, e.g., as used in legacy surgical environments 100A. In contrast, FIG. 1B is a diagram showing an example surgical environment 100B of the integrated surgical navigation and visualization system, according to an example embodiment of the present disclosure. As shown in FIGS. 1A and 1B, the example surgical environment 100B of the present disclosure includes the integrated surgical navigation and visualization system 101C, whereas the legacy environment 100A typically includes a surgical navigation system 101A separate and distinct from the surgical visualization system 101B. In some aspects, the separated surgical navigation system 101A and the surgical visualization system 101B may be communicatively connected via cable 166, providing limited options for augmented reality during surgery. The integrated surgical navigation and visualization system 101C of FIG. 1B and/or the legacy surgical visualization system 101B of FIG. 1A may include a digital surgical microscope (DSM) head 110 mounted on a robotic arm 120. To enhance robotic arm reach, the robotic arm 120 may be mounted on an extension platform ("diving board") 130. To extend the range of orientations in which the integrated surgical navigation and visualization system can be used, the DSM head 110 can be mounted on a "universal" coupler 140, which may provide one or more additional degrees of freedom beyond the end of the robotic arm.

In some embodiments of the present disclosure, a force-torque sensor 150 may be incorporated into the robotic arm-DSM head combination (e.g., of the integrated surgical navigation and visualization system 101C). The force-torque sensor 150 may allow users to pose the DSM head at will using physical actions (e.g., as legacy microscopes). For example, the user can physically grab some part or parts of the DSM head or handles attached or otherwise coupled to the robotic arm, and can direct the head toward the desired pose. The force-torque sensor 150 can detect the physical input. A software control module can convert the force-torque sensor's output into an intended change in pose. The same or an additional control module can convert such user intent into a set of robot pose changes that can be streamed to the robot to effect the changes.

The integrated surgical navigation and visualization system 101 and/or the legacy surgical visualization system 101B may further include a cart 154. The cart 154 can provide a support structure for the robotic arm and diving board. Furthermore, the cart 154 may include an embedded processing unit (EPU) 160 and power management unit with uninterruptible power supply (PMU/UPS) 162. The EPU 160 can communicate with the DSM head, sending commands and receiving command responses and image and status data. The PMU/UPS 162 can manage power for the system 101. The uninterruptible power supply (UPS) 162 can provide the user with the option to unplug the cart for a short time to reposition if needed. The PMU/UPS 162 can also provide the surgeon with an option to have a short time to transition to backup equipment should the hospital power fail.

Imagery can be captured by the digital surgical microscope's optics and image sensor electronics (not shown), sent to the EPU, processed and sent to the three-dimensional (3D) stereoscopic display 170. The 3D stereoscopic display 170 may be mounted on an articulated display mounting arm 180, and its pose may be controlled by display pose adjustment handle 182 e.g., to allow the user to pose the display for optimal viewing quality and comfort.

The surgeon 190 may wear 3D glasses 192 to view the 3D stereoscopic display. The 3D glasses 192 may provide the surgeon to view a 3D stereoscopic view of surgical site 194. Zoom and focus optics in the digital surgical microscope can be controlled by the user, and can provide 3D stereoscopic focused views of the surgical site over a range of working distances (e.g., 200 millimeters (mm)-450 mm) and magnifications (e.g., 3×-11×). In some embodiments the 3D glasses are passive wherein the polarizing film on each respective lens of the glasses left and right are respective conjugates to polarizing film applied to every other line on the display (e.g. the left glasses lens passes the even-numbered lines of the display and block the odd-numbered lines, and vice-versa.). In some embodiments, the 3D glasses are active shutter types synchronized to the display such that the left eye passes e.g. every other time-sequential frame shown on the display and blocks the remainder and the right eye performs the complement. In some embodiments, the 3D display may be "glasses-free" and may provide 3D display to the user without need for 3D glasses.

As used herein, "working distance" and "focus" may be used interchangeably. Furthermore, the user interface of the integrated system 101C may refer to working distance as the variable parameter. When a change is made to the desired working distance, the optics move such that the focus distance changes. Thus, the distance between the microscope and the focus surface may change, and that distance can be generally considered to be the working distance.

The integrated surgical navigation and visualization system 101C and/or the legacy surgical navigation system 101A may include a navigation camera ("navigation localizer" or "localizer") 200. For example, in the legacy surgical navigation system 101A shown in FIG. 1A, the navigation localizer 200 may be mounted on the articulated localizer mounting arm 202. The navigation localizer 200 may be user-poseable by localizer pose adjustment handle 204.

A navigation-trackable patient reference target 230 can be mounted rigidly to a patient clamp (e.g. a "Mayfield" clamp) 240. The patient clamp 240 may be mounted near surgical bed 242 where the patient 250 resides. The patient clamp 240 may avoid areas of the patient's anatomy to move in relation to the patient reference array.

The digital surgical microscope may be rendered to be compatible with (e.g., by being rendered trackable by) the localizer with the addition of the DSM navigation target (e.g., "shellmet," as derived from "shell" and "helmet.") 210. Various styles of navigation targets can be used with the system such as the retro-reflective spheres shown schematically in the Figure or image-based corner targets described elsewhere in this document.

The localizer may detect the pose in some reference frame of compatible devices (i.e. trackable devices, navigation targets) in its viewing space. The localizer may supply this information to the EPU responsive to requests for such information in a quasi-real-time fashion (e.g., 15 times per second in a "polling" method) or at a constant rate even without requires (a "broadcast" method). Typically, the reference frame in which the poses are reported may be that of the localizer. In some implementations, however, pre-calculations may be performed in order to report the poses from a different reference frame.

Relevant rigid patient anatomy such as the skull may be mounted to or accessible via, clamp 240. Systems and methods described herein may guide the user through a patient anatomy registration procedure, as part of the preparation workflow. This registration procedure can determine the pose of the patient data 270 relative to the navigation target affixed rigidly either directly or indirectly to the relevant patient anatomy.

In some aspects, the integrated surgical navigation and visualization system 101 may comprise a navigation system integrated into the DSM head I 02, which may be mounted on robotic arm 120. The cart 154 may support the robotic arm 120 as well as a boom-mounted 3D stereoscopic display (e.g., 3D stereoscopic display 170) and a mast-mounted touchscreen 171 for user input. Additional displays can also be connected optionally.

The integrated surgical navigation and visualization system 101 may provide 6 degree of freedom (6DoF) position and orientation information of the head relative to some reference or target viewable by the navigation device in the scene. The digital surgical microscope may provide stereoscopic visualization over a range of magnifications (typically 1×-9×) and a range of working distances (typically 200 mm-450 mm.)

An objective of surgical navigation may include guiding the surgeon around the patient's anatomy during a surgical procedure so that the surgeon can complete the procedure in the most effective, least damaging way. The patient's anatomy has typically been scanned in a device such as a computed tomography (CT) machine or a magnetic resonance imaging (MRI) machine, and the results may be stored in a format such as a stack of image "slices" of the anatomy from which the 3D anatomy can be reconstructed and explored. The above described objective can thus achieved by providing a view or views of various levels of relative position and orientation information between the patient data and various objects such as a navigation probe and/or the digital surgical microscope's optical axis.

II. Levels of Navigation Complexity

There may be various levels of complexity for surgical navigation, each with increased costs and benefits. Each level of complexity may involve increased complexity in camera calibration while each proving more navigation information (or more readily used such information.)

A simple form of navigation may be to provide in such a view the location in the patient data of a single point such as the tip of a navigation probe. The next level of complexity may involve showing a vector in the data, where the vector may represent the line along which the axis of the navigation probe lies. The next level of complexity may include showing the correct orientation of the probe about that vector.

At higher levels of complexity, surgical navigation may be integrated with visualization.

For example, the next level of complexity may be to provide vector with orientation for a digital surgical microscope, with the probe vector becoming the optical axis of the microscope. The probe tip may become a focal point of the microscope, and the orientation information may pertain to the "up" direction of the onscreen display of the microscope (e.g. the vertical dimension of the microscope display.) At this level of complexity, a view of a given two-dimensional "slice" of the patient 3D data largely similar to the onscreen live view of the digital surgical microscope is possible.

A higher level of complexity for navigation achieved in various embodiments described herein is to overlay a rendering of such a two-dimensional "slice" of the patient scan data over the live microscope image, and have visible features of the rendering align to their corresponding features in the live view to some level of accuracy and to enable movement of the "slice" along the optical axis, for purposes of "x-ray vision" to view structures beneath the current physical surface of the patient's anatomy. An even higher level of complexity for navigation also achieved in various embodiments described herein is to provide a three-dimensional rendering (albeit to the two-dimensional display) of the patient scan data over the live view, and have corresponding features align.

III. Determining the Relative Pose of an Object and the Patient Anatomy

Each level of complexity of surgical navigation may involve a determination of relative position and/or orientation of one object relative to another. In one embodiment, the highest level of surgical navigation complexity described herein may comprise all the described levels of complexity. Therefore, for ease of explanation, the highest level is described (e.g., via FIG. 1C).

Figure 1C:
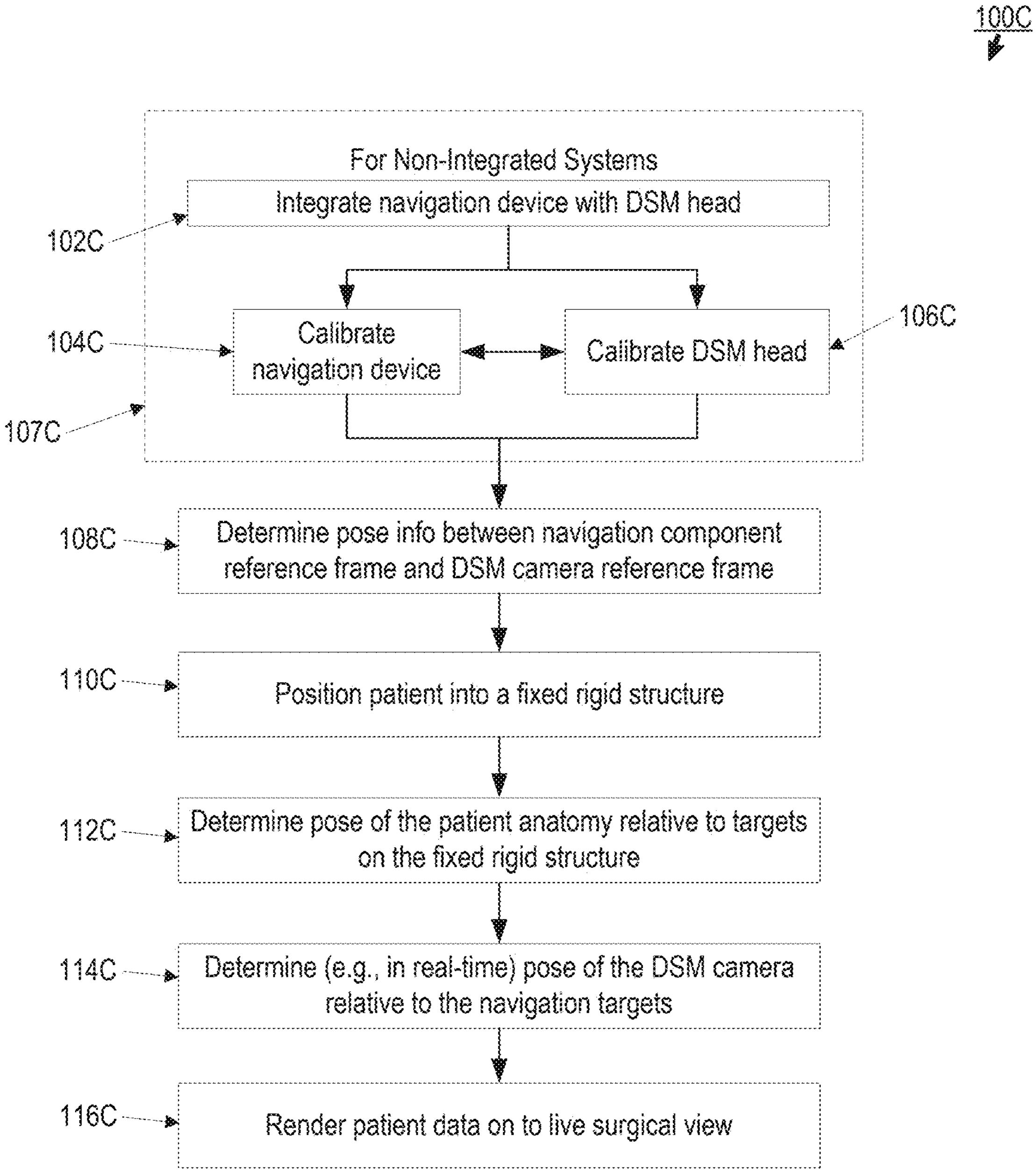
FIG. 1C is a flow diagram showing an example process for determining the relative pose of an object and the patient anatomy (e.g., in an integrated surgical navigation and visualization system), according to an example embodiment of the present disclosure.
Figure 1D:
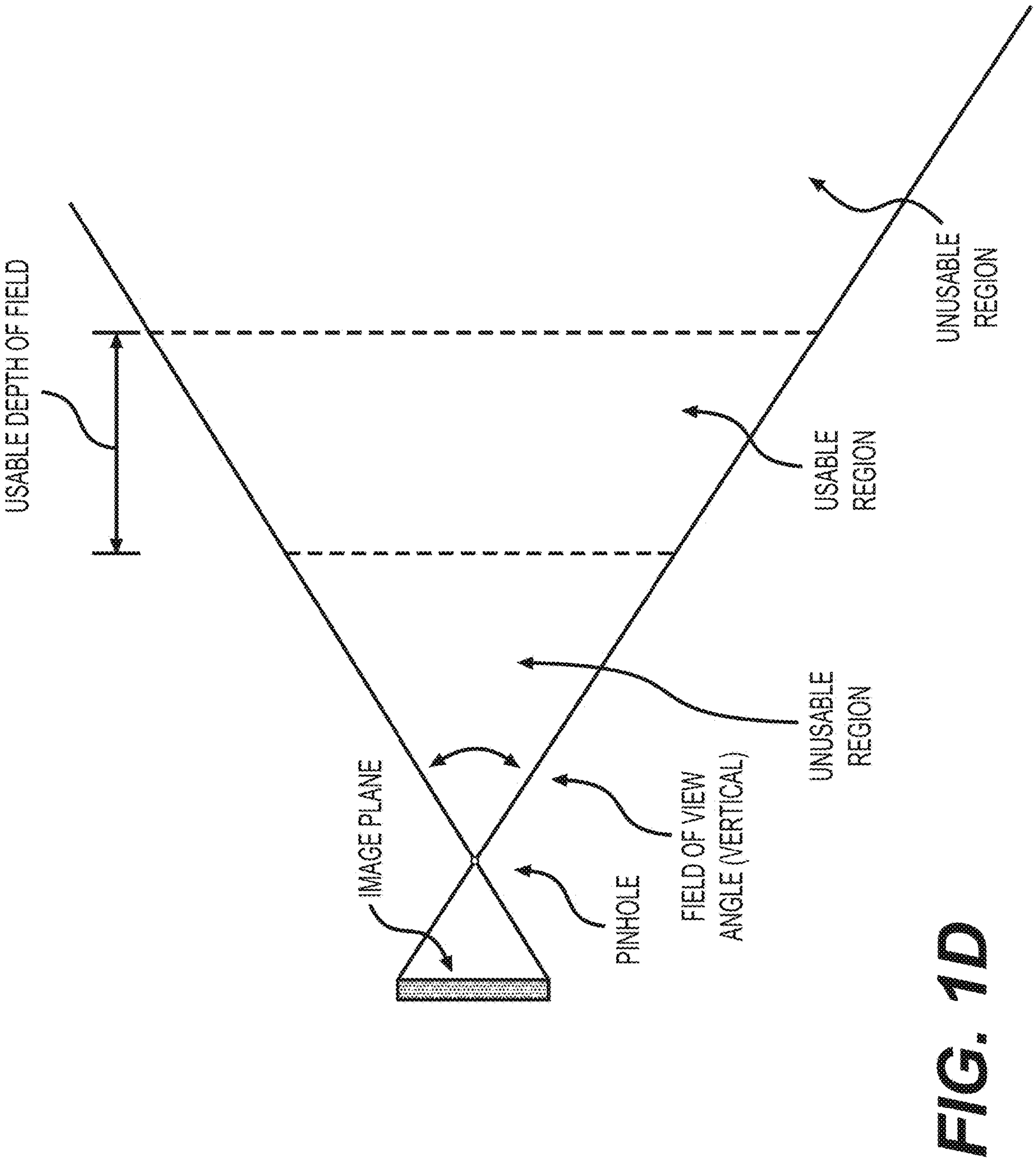
FIG. 1D is a diagram showing an example pinhole camera vertical field of view angle, according to a non-limiting embodiment of the present disclosure.

FIG. 1C is a flow diagram showing an example process 100C for determining the relative pose of an object and the patient anatomy (e.g., in an integrated surgical navigation and visualization system (e.g., a high level of complexity)), according to an example embodiment of the present disclosure. In one embodiment, process 100C may begin with integrating a navigation device into the digital surgical microscope head (102C). Furthermore, the navigation device and the digital surgical microscope camera(s) may each or collectively be calibrated (steps 104C and 106C, respectively). However, as systems that already integrate surgical navigation and visualization are described herein, steps 102C through 106C may be optional (e.g., as shown by marker 107C. For integrated surgical navigation and visualization systems, process 100C may begin at a subsequent step shown in FIG. 1C.

For example, process 100C may begin with the navigation component of the integrated surgical navigation and visualization system determining the relative position and orientation information (also known as "pose" information) between the navigation component reference frame and the reference frame of the digital surgical microscope camera(s) (step 108C). This step may be optionally combined with calibration steps previously described.

The patient may be positioned into a fixed rigid structure such as a clamp (step 110C). The targets on the clamp may be provided with poses, such that the targets may be detectable in real-time or near real-time by the integrated surgical navigation and visualization system and associated methods.

The pose of the patient anatomy m the preoperative, perioperative and/or intraoperative (typically 3 d) patient data scan relative to the target(s') reference frame(s) on the fixed rigid structure (e.g., clamp) may be determined (step 112C). By including a calibration target fixed rigidly to the patient clamp, this step may be optionally combined with the determination of relative pose between the navigation device reference frame and the reference frame of the digital surgical microscope camera(s). Also or alternatively, step 112C may be combined with the calibration of the digital surgical microscope camera(s). The calibration target may be used as a navigation target.

At step 114C, the pose of the DSM camera relative to the navigation targets may be determined (e.g., in real time or near-real-time). For example, the navigation component of the integrated surgical navigation and visualization system may be used to view the targets on the clamp in real-time or near real-time to provide the latest pose of the digital surgical microscope camera(s) relative to the navigation targets. Thus, using data collected in the previous steps, the pose of the digital surgical microscope camera(s) relative to the patient data may be calculated.

At step 116C, the patient data for use by the surgeon may be rendered with the varying levels of surgical navigation complexity described previously either alongside or overlaid onto the live surgical view.

IV. Navigation Device

The navigation device may provide 6 degree of freedom (6DoF) position and orientation information of the head relative to some reference or target viewable by the navigation device in the scene. The navigation device may be realized using a standard imaging device such as a USB webcam. This monoscopic camera may be used to view the scene and provide the scene image in digital form to a main information processor module which uses standard image processing techniques to detect all of the navigation targets present in the scene. Further standard image processing techniques may be used to calculate the 6 DoF position and orientation information of the given navigation target relative to the camera reference frame.

The resolution of the camera(s) used in the navigation device may affects accuracy. For example, a higher resolution camera can provide higher resolution position and orientation measurements for a given measurement space compared to a lower resolution camera. The measurement space may be measured at a higher spatial frequency. For example, a camera using an image sensor with 1920 pixels in the horizontal direction measuring a space that is 1.92 meters (1920 mm) wide will sample that space at 1920 pixels/1920 mm=1 pixel per mm. A camera with sensor having 3840 pixels in the horizontal direction will sample that space at 3840 pixels/1920 mm=2 pixels per mm. When optics are designed correctly to match the sensor pixel size, this space-sampling resolution increases directly proportionally with the resolution of the sensor used in the camera.

Sub-pixel resolution techniques such as used in OpenCV::comerSubPix( ) can dramatically improve this resolution for a lower resolution camera and known (or algorithm-friendly) target patterns but can also be used for the higher resolution camera, thereby retaining the advantage of the higher resolution camera.

The field of view of the navigation camera as used here means the angular span viewable by the camera in both the horizontal and vertical directions. The usable region within that three-dimensional region relates to the depth of field of the camera optics in which items are enough in focus to be usable; we might use the term "depth of field" for this definition of usable region, which may differ slightly from traditional imaging because the target detection computer vision algorithms can often use images successfully that are blurrier than might be considered usable by a human viewer.

The field of view may need to be large enough to accommodate all uses of the device; the navigation targets may be required to be in view at all times. Additionally, workflow requirements dictate that the system support use of tools that are typically used without the microscope viewing them, such as a navigation probe. Such a probe is used after patient registration to the navigation system, before the patient is opened, to determine the optimal surgical approach. Some systems require the use of the probe to perform the registration step. The navigation system of the present application offers an improvement over using a probe for registration.

The prevailing and most straightforward method of modeling an optical system for camera calibration is the pinhole model in which the camera is modeled as a simple pinhole camera. However this does not fully match a real system because a pinhole camera has an infinite depth of field. That is, every object in the scene is always in focus regardless of its distance from the camera. In a real camera there is a usable region in the field of view in which objects are sufficiently in focus; objects outside of that range are too blurry for use.

FIG. 1C is a diagram showing an example pinhole camera vertical field of view angle, according to a non-limiting embodiment of the present disclosure. As shown in FIG. 1C, the vertical field of view angle includes usable region relating to the depth of field.

A trade space is constructed to determine the optimal values of field of view, depth of field, and camera resolution for the application. Each affects the usability of the system and the measurement accuracy of target position and orientation, and camera resolution directly affects the cost of goods and computational load.

To increase robustness of the system, a light source such as pulsed LEDs is optionally added to the navigation camera device. The lighting faces the scene and is only seen by the navigation camera when it reflects off of items in the scene, particularly the navigation targets. Optical filtering is optionally added in front of the camera lens (and optionally in front of the LEDs) which filters are matched to the wavelengths of the lighting used such that light outside the desired spectrum is rejected.

Additionally, the lighting is optionally pulsed in a pattern synchronized to the navigation camera sensor such that the camera can reject spurious background lighting. For example the LEDs are turned OFF for the exposure time of the even frames of the navigation camera (frame 0, frame 2, frame 4 etc.) and turned OFF for the odd frames (frame 1, frame 3 and so on), then then an OFF frame is subtracted from its nearest ON frame (for example the ON frame that arrived just prior) . . . this "background suppression via light synchronization method" suppresses background lighting and shows largely only the reflections of the LED light source.

This method suffers from the problem of reflection of the LED light source from objects other than the navigation targets. However, with image processing to detect the a priori known target patterns from the resultant navigation cam images, this method still works sufficiently.

Further robustness is achieved by optionally using targets that fluoresce in one region of the electromagnetic spectrum upon stimulation by energy from a different region of the spectrum: The light source and any required optics and optical filters for the light source are designed to generate and project to the scene the stimulation region of the spectrum; the targets are designed to absorb this stimulation and emit the emission region of the spectrum; and the optical filter in front of the camera is designed to pass just the emission region of the spectrum. When used with the "background suppression via light synchronization method" described above, the resultant navigation camera image contains largely only images of the navigation targets; reflections of the navigation LED light stimulation from objects other than the navigation targets are suppressed considerably.

V. System Pipeline

Figure 2:
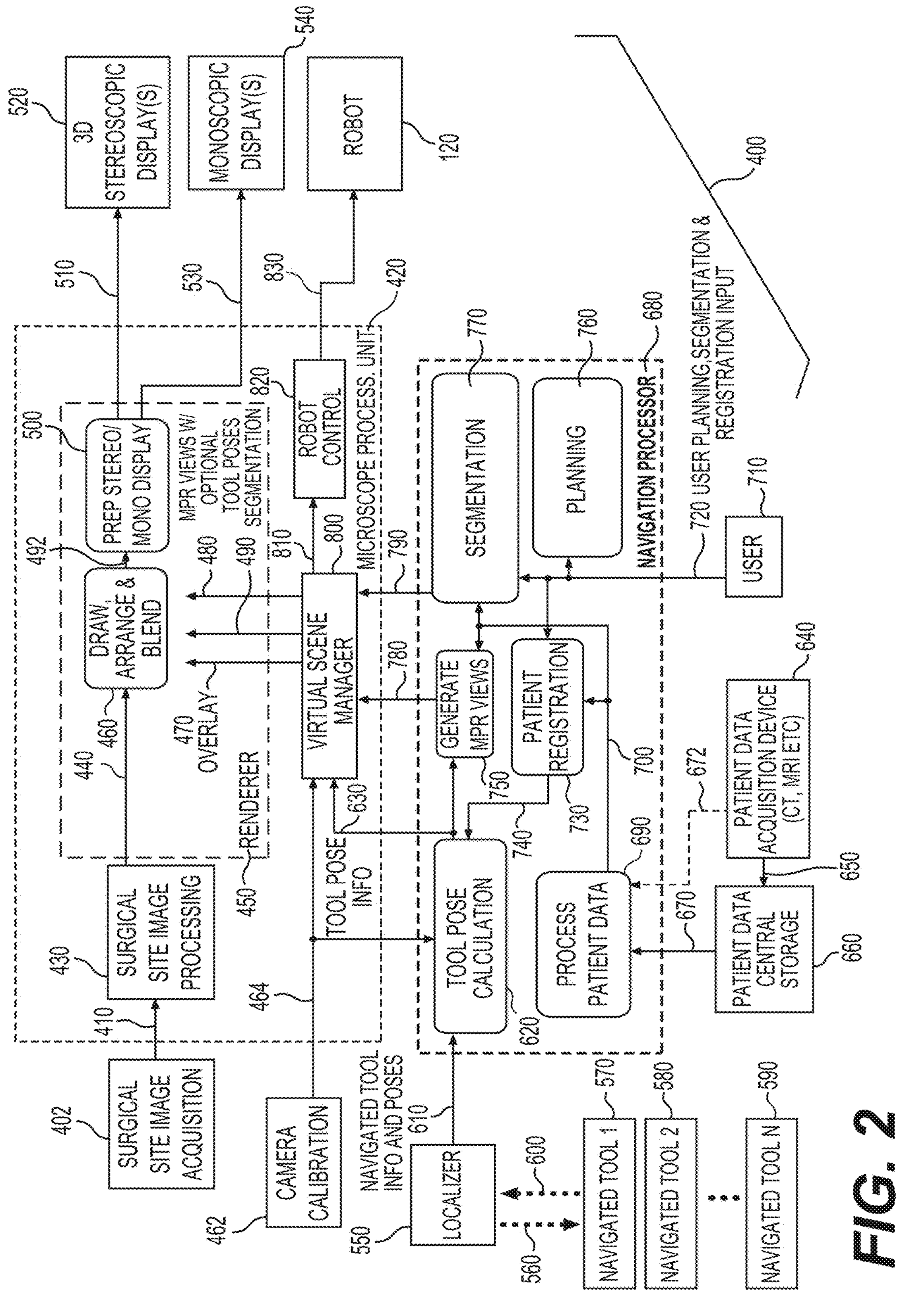
FIG. 2 is a flow diagram showing an example pipeline for the integrated surgical navigation and visualization system, according to an example embodiment of the present disclosure.

FIG. 2 is a flow diagram showing an example pipeline 400 for the integrated surgical navigation and visualization system, according to an example embodiment of the present disclosure. Furthermore, pipeline 400 describes one or more examples of how surgical visualization and navigation information is generated, captured, processed and displayed in the integrated surgical navigation and visualization system 101. It is understood that while the processes associated with pipeline 400 are shown as near-linear, one or more processes can happen concurrently and/or in a different order than is presented here.

Pipeline 400 may begin with image acquisition of a surgical site (block 402) (e.g., as part of an image data stream). The surgical site image acquisition may occur at or be performed by a surgical site image acquisition module. An example image acquisition module of a fully featured stereoscopic digital surgical microscope, including light source(s), zoom and focus optics, image sensors and all supporting electronics, software, firmware and hardware, is further described in U.S. Pat. Nos. 10,299,880 and 10,334,225, the entireties of which are hereby incorporated by reference herein. This image acquisition module may generate surgical site image data stream 410, which may be communicated to microscope processing unit 420 and the associated surgical site image processing module 430. Images may be captured and processed at a frame rate high enough to be perceived as video by the user, for example, 60 frames per second (fps.). Thus, images may be considered to be "image data stream." It is to be understood that, where a two-camera stereoscopic digital surgical microscope is described, the concept may be extendible to an N-camera digital surgical microscope where N is 2 or greater.

The surgical site image processor may process the image data 410 received from the surgical site image acquisition module, and may produce processed image data stream 440.

The processed image data stream 440 may be sent to the renderer module 450, and more specifically to the draw, arrange & blend module 460. The renderer module 450 may also receive camera calibration information 464, which may be generated in an offline process. Methods and systems for producing camera calibration information are further described in U.S. Pat. Nos. 9,552,660 and 10,019,819, the entireties of which are hereby incorporated by reference herein. Camera calibration information may be generated for each "eye" of the stereoscopic digital surgical microscope. The camera calibration may provide the renderer module with the option to set up its virtual cameras such that, along with proper navigation data to be described, rendered overlay objects appear in similar perspective, size (magnification) and pose as objects captured by the surgical site image acquisition module. For example, the rendered overlay of a portion of a patient's skull and skin may appear in a similar perspective and pose as a live view of the same portion through the digital surgical microscope.

Such combination may continue in the draw, arrange & blend module 460, where surgical site processed image data stream 440 may be combined with patient data overlay 470, multiplanar reconstruction (MPR) views with optional tool poses 480, and segmentation information 490 into a raw stereoscopic rendered image stream 492. The raw stereoscopic rendered image stream 492 may be sent to the stereoscopic/monoscopic display preparation module 500. The stereoscopic/monoscopic display preparation module 500 may transform the raw stereoscopic rendered image stream 492, as necessary, into the final stereoscopic display output data stream 510 required by the stereoscopic display(s) 520. Different stereoscopic displays may require different final stereoscopic data formats, which the display preparation module may provide. Also or alternatively, there may be one or more monoscopic displays 540. The various data formats 530 associated with the monoscopic displays 540 may also be provided via configuration by the display preparation module.

The preceding few paragraphs discuss the acquisition of a live surgical site image stream, its processing and combination with navigation module output and the display thereof. The navigation module output is formed as follows.

The localizer 550 may comprise a sensing device having a certain scene visible to its field of view. The scene may depend on the design of the device and pose of the device. In some embodiments, the localizer 550 may send a communicative query 560 to one or more navigated tools. The navigated tools, which might be present in the scene, may include, for example, a first navigated tool 570, a second navigated tool 580, and/or up to a certain number of such tools 590. Such a communicative query in some embodiments may involve directing infrared light either at a constant level or in a known pulse rate and/or sequence toward the scene. In some other embodiments, the query may be of a passive nature, such as relying on ambient visible light to illuminate a high-contrast pattern formed on the navigated target(s). Control of this infrared light (e.g., by switching on and off, or by selecting a specific wavelength) may help avoid illumination interference with the digital surgical microscope fluorescence capabilities.

The communicative query may be sent back as a response 600 from each respective navigated tool. The response may be received by the localizer, and may be sent as tool information and pose information 610 for each navigated tool. The localizer may run these query and/or responses as send/receive cycles at real-time or near real-time rates such as 15 Hertz (Hz) to 30 Hz. The pose information for each tool may be determined in a common space for all tools. For example, a coordinate reference frame origin and orientation relative to a rigid feature of the localizer may be the common space that is used. The tool and pose information 630 may be received by tool pose calculation module 620.

In an offline process, a patient data acquisition device (CT, MRI, etc.) 640 may be used to scan the relevant anatomy of patient 250 to generate acquired patient data 650. The acquired patient data may be optionally stored in a patient data central storage 660. The patient data may be sent (e.g., from the central storage 670) to the navigation processor 680. Alternatively, the patient data may be sent to said processor as patient data 672 directly from acquisition device 640.

It is understood that the physical location of each navigation processor, the microscope processing unit and all other main components may vary with implementation. Generally, the microscope processing unit 420 and the navigation processor 680 may reside in the embedded processing unit 160, but this is not a requirement. For example, the navigation processor might be physically located inside the same housing as the navigation camera, remote from the cart which might house the embedded processing unit.

The patient data processing module 690 may process the patient data into format(s) needed by various modules in the rest of the system as processed patient data 700.

Figure 4:
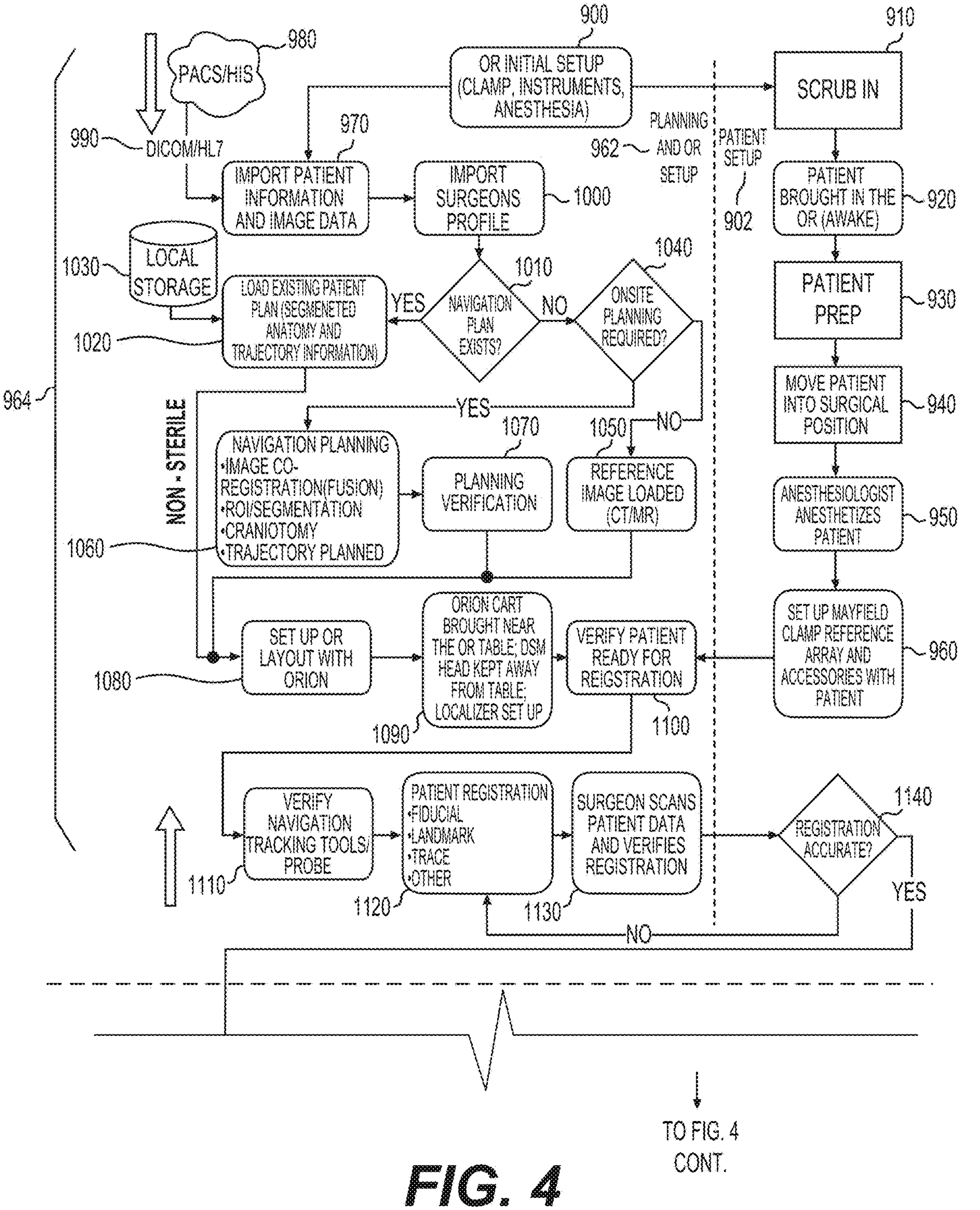
FIG. 4 is a flow diagram showing an example workflow performed for the integrated surgical navigation and visualization system, according to an example embodiment of the present disclosure.
Figure 4:
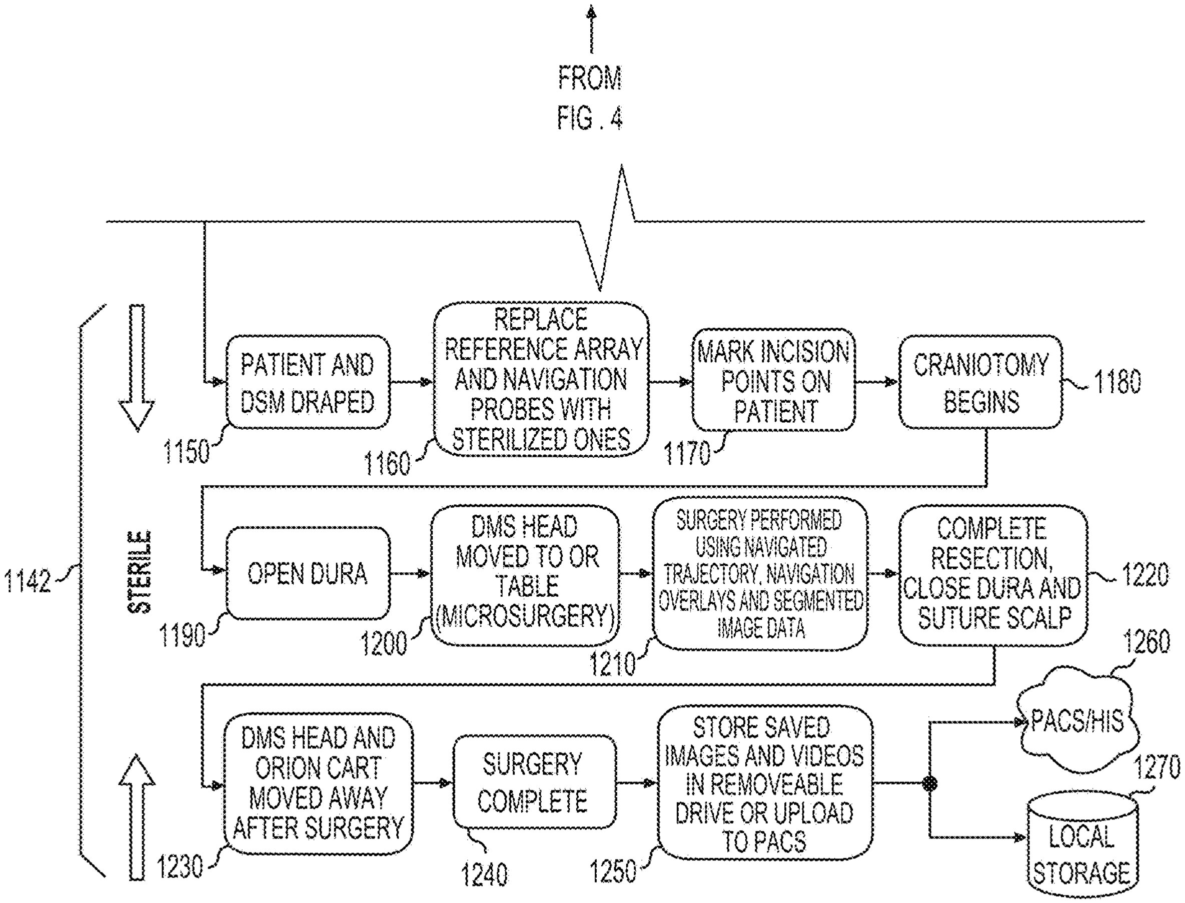
Figure 5A:
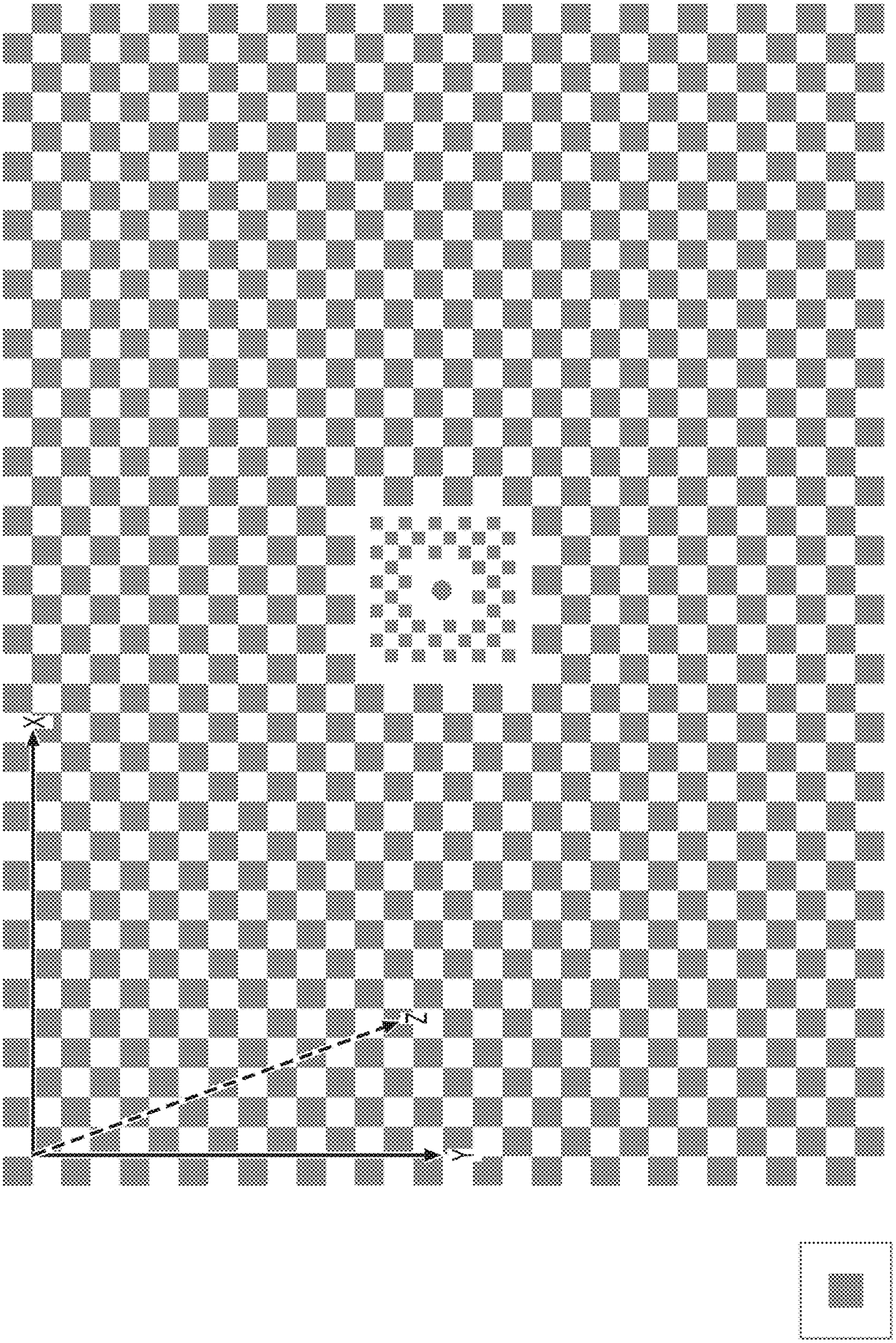
FIG. 5A is a diagram illustrating an example calibration reference frame setting the origin and axes, according to an example embodiment of the present disclosure.
Figure 5B:
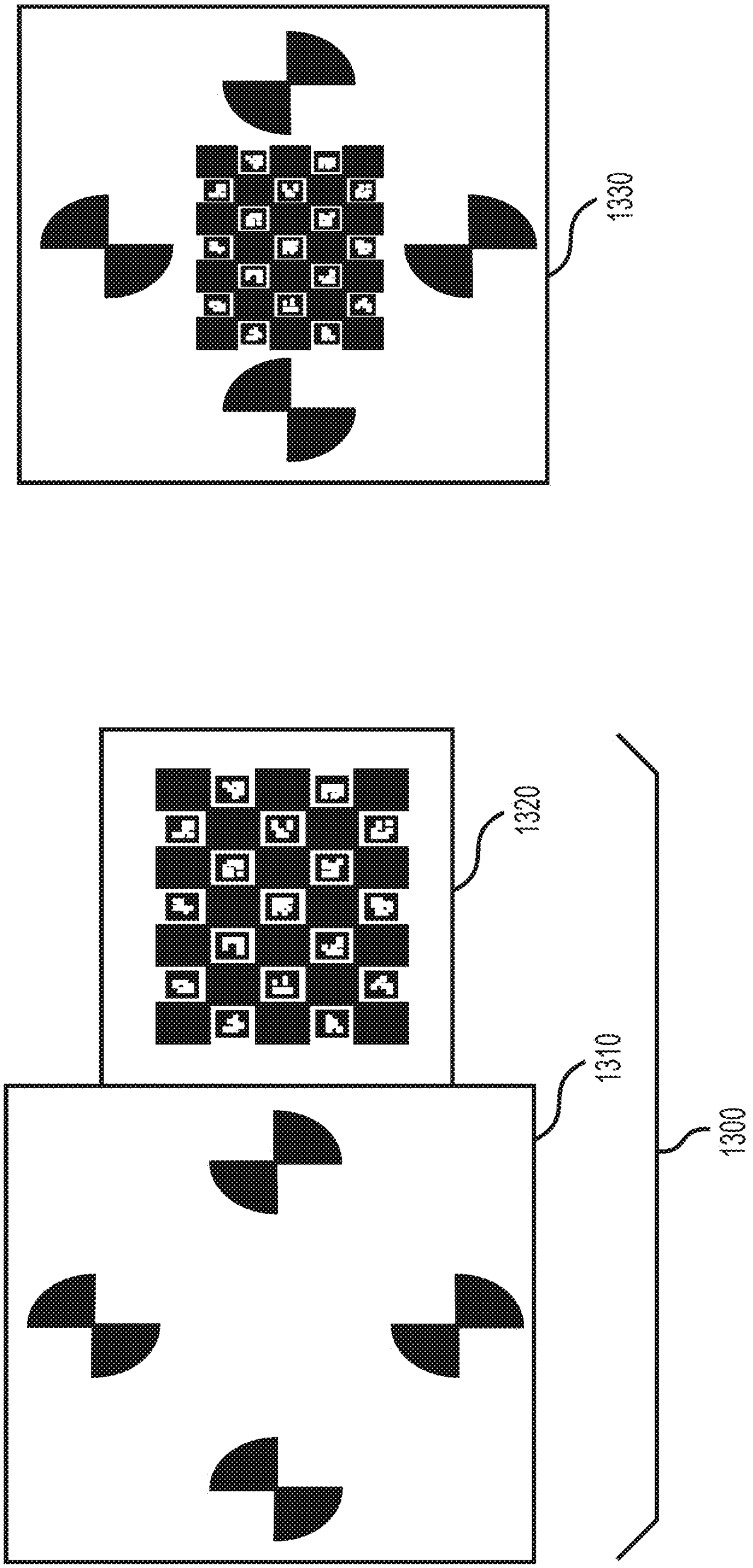
FIG. 5B is a diagram illustrating a calibration object applicable to the integrated surgical navigation and visualization system, according to an example embodiment of the present disclosure.

The relative timing of processes associated with this pipeline is further described in relation to FIG. 4. As will be described below, the user 710 may direct the software via user planning, segmentation and registration input 720 to perform those respective workflow steps. The patient registration module 730 may direct the user and accept user input to generate patient registration information 740. The registration information 740 may describe the pose relation between the processed patient data 700 and the patient reference navigation target 230.

Use of the processed patient data 700 may continue as the multiplanar reconstruction view generator 750 generates multiplanar views 780. The multiplanar views 780 may assist the user in the use of the planning module 760 to generate opening, approach and objective patterns and trajectories (as standard features in surgical navigation systems). In some embodiments, a 3D view generator may further assist the user in such endeavors, e.g., by generating a 3D representation of the patient data. The view of the 3D representation can be adjusted based on a desired pose and/or scale.

The multiplanar views 780 and/or any 3D representation of the patient data may assist the user in use of the segmentation module 770 to generate segmented geometry 790. For example, if the patient pathology is a tumor located in some certain location of the patient's brain, the segmentation module 770 provides the user the option to isolate the tumor in the patient data such that the segmented geometry represents the tumor in size, shape and pose.

One or more of the camera calibration information 464, tool pose information 630, multiplanar reconstruction views 780, 3D representation of the patient data, and segmented geometry 790 may be provided to the virtual scene manager 800. The virtual scene manager 800 may generate representations of the patient data overlay 470, multiplanar reconstruction views with optional tool poses 480, and segmentation information 490 usable by the draw, arrange & blend module 460 in various ways, as configured by the user.

For example, the overlay may be displayed at a distance along the optical axis of the digital surgical microscope, with an on/off option available. Also or alternatively, said distance along the optical axis is may be controllable by the user, allowing an "X-ray vision" of patient data beneath some portion of the patient anatomy.

In existing conventional systems, where the overlay is injected into traditional optical microscopes, the focal plane of the overlay display is distinctly one single plane whereas the view of the scene is an analog collection of many focal distances. In such conventional systems, users are often forced to refocus their eyes when switching between viewing the live surgical site and viewing the overlay. Further the perceived location of that one single overlay display plane is often located significantly away from the general surgical site scene, for example a few centimeters above the site. However, systems and methods described herein may allow the overlay information to be presented on the same display focal plane as the stereoscopic view of the live surgical site.

While there may be a single display focal plane of the stereoscopic view of the live surgical site (e.g., the plane of the stereoscopic display), the user may still perceive a full or perceptually full analog collection of many focal distances owing to the wonders of the human visual system.

Further to the example, one or more (or all) of the three multiplanar reconstruction views plus a 3D representation may optionally be displayed at the side of the main display screen, thereby integrating, in one display, the live surgical view along with the navigation information. This integration is yet another benefit over existing multi-device systems, which often force the user to look back and forth between the visualization system and the navigation system, mentally carrying a large informational load between the systems.

VI. System Preparation

Figure 3:
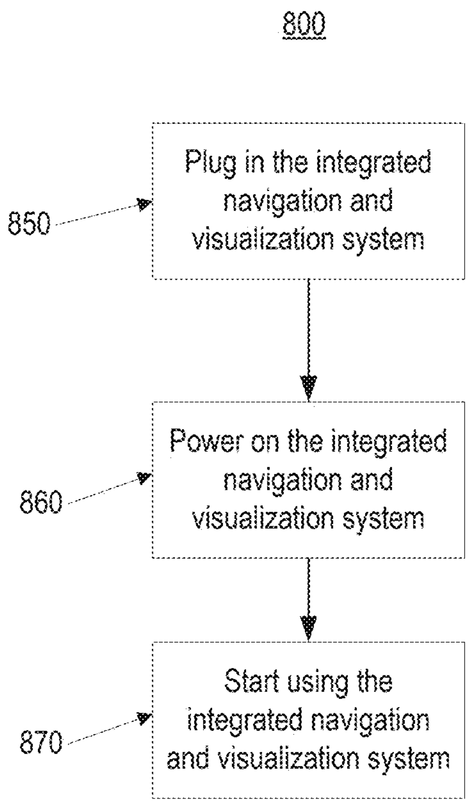
FIG. 3 is a flow diagram showing an example process for starting up the integrated navigation and visualization system, according to an example embodiment of the present disclosure.

FIG. 3 is a flow diagram showing an example process 300 for starting up the integrated navigation and visualization system, according to an example embodiment of the present disclosure. For example, the user of the integrated navigation and visualization system may be trained to follow system preparation steps as shown in process 300. At step 850, the user may plug the integrated navigation and visualization system into the hospital main power (e.g., by plugging into a wall socket). At step 860, the user may power the system on (e.g., by turning the "on" switch). At step 870 the user may begin using the system. Workflow steps after turning on the system are further described below, in relation to FIG. 4.

The relative ease of starting up the integrated navigation and visualization system, as illustrated in FIG. 3, confers a major advantage of the integrated surgical navigation and visualization system over conventional multi-component systems for navigation and visualization, as the integrated surgical navigation and visualization system eliminates or obviates the need to perform various setup steps or startup processes. For example, as shown in FIG. 3, a single power plug may be required to be connected to hospital mains, whereas conventional multi-component systems may typically require at least two such connections. Furthermore, physical connections need not be made by the user between the navigation system and the visualization system. In contrast, conventional, multi-component systems may typically require some form of connectivity between the separate navigation system and visualization system. Furthermore, workflow synchronization need not be made between the navigation system and the visualization system. In contrast, conventional, multi-component systems may require some form of such workflow synchronization.

VII. System Workflow

FIG. 4 is a flow diagram showing an example workflow performed for the integrated surgical navigation and visualization system, according to an example embodiment of the present disclosure. A software application on the integrated surgical navigation and visualization system may perform software portions of the pipeline and may provide a workflow for the user to follow. Various portions of the workflow may be implemented in a workflow command and control module while other portions may be performed outside of the software and outside of the system. Such portions may be presented in order to provide a full picture of system usage.

For clarity, workflow command and control module is not shown in the data acquisition, processing and display pipeline 400. The implemented workflow is described herein. It is understood that while this workflow is described in a near-linear fashion, some processes can happen concurrently and/or in a different order than is presented here.

The workflow may begin with a set up of the operating room ("operating room setup") 900, where equipment, tools and accessories may be brought into the operating room. Such equipment, tools, and accessories may include, but are not limited to, the integrated surgical navigation and visualization system, patient clamp(s), navigation tools, surgical instruments, and anesthesia equipment. A group of workflow steps considered as the patient setup workflow steps 902 may be undertaken by operating room staff These steps may begin with a scrub in 910, where staff who enter the sterile field perform their pre-cleaning and entry into sterile clothing. Additionally some preliminary patient scrub may be performed at this time.

At step 920, the patient may be brought into operating room awake. Afterwards, step 930 may include patient preparation 930, which may involve include hair removal near the surgical site and further sterilization of the nearby area. At step 940, the patient may be moved into a surgical position and at step 950, the anesthesiologist may anesthetize the patient.

Portions of the navigation setup associated with the patient may be performed in step 960. In some aspects, the relevant anatomy of the patient may be fixed rigidly relative to the navigation reference target. In neurosurgery, for example, the patient's skull may be fixed rigidly into a Mayfield clamp and the navigation reference target fixed rigidly to the clamp. Accessories, such as a navigated probe, may be made available at this time, for example, by removing them from their sterilization kit and placing them on a sterile table to be available for the surgeon.

The workflow may progress to a set of steps referred to herein as planning and operating room setup 962. Of the steps associated with planning and operating room setup 962, a steps 964 may typically occur in the non-sterile realm of the operating room, e.g., with equipment that is not required to be sterilized.

The user may proceed to use the software application on the integrated surgical navigation and visualization system to import patient information and patient image data at step 970 from patient data central storage. In some aspects, the patient data central storage may comprise one or more of a picture archiving and communication system (PACS), a hospital information system (HIS), or a radiology information system (RIS), collectively referred to as PACS/HIS/RIS 980. The patient information and patient image data may be provided over a communications interface such as hospital ethernet as formatted patient data 990. The patient information and/or patient image data may be formatted using one or more options (e.g., Digital Imaging Communication in Medicine (DICOM), Health Level (HL7), etc.).

At step 1000, the surgeon profile may be imported. Alternatively, a surgeon profile may be created, e.g., if none exists. At decision step 1010, if a navigation plan exists, then at step 1020 the user may load existing patient plan (segmented anatomy and trajectory information) from local storage 1030. However, if no navigation plan exists, the user may determine whether onsite planning is required at decision step 1040. If a navigation plan does not exist and/or if no onsite planning is otherwise required, then a reference image may be loaded at step 1050. If navigation planning is required or desired, then at step 1060 navigation planning may be performed. Additional steps for navigation planning may include, for example, image modality co-registration or fusion (e.g., for registering MRI to CT), region of interest (ROI) specification, segmentation of one or more regions, craniotomy (in the case of cranial neurosurgery) or other approach specification, and trajectory planning. At step 1070 the navigation planning may be verified, e.g., by the lead surgeon.

At step 1080, the operating room layout may be determined. The operating room layout may involve a positioning and/or an orientation of the integrated surgical and navigation visualization system, and how various pieces of operating room equipment are to be posed at various phases during the procedure.

At step 1090, the integrated surgical navigation and visualization system may be brought near an operating room table where the patient resides. The digital surgical microscope head may be kept away from sterile field for now. The localizer may be posed such that it can "see" (e.g., receive within its field of view), the relevant navigated tools needed during the current workflow steps. For example, during registration, the localizer may need to see the navigated hand probe and the navigated patient reference target.

At step 1100, the user may verify that the patient is ready for registration. At step 1110, the user may verify that the localizer is tracking the tools needed for registration. In some embodiments, these tools may include the navigated hand probe and the tracking may involve locating the navigated patient reference target. In other embodiments, the tracking may involve locating the navigated target(s) on the digital surgical microscope and the navigated patient reference target.

At step 1120, a patient registration may be performed. Various forms of registration may be available in the surgical navigation visualization system. A chosen registration may be a function of several variables, including but not limited to a type of procedure, patient position, and/or a patient condition. Forms of patient registration available may include, for example, fiducial matching, landmark matching, and trace.

In fiducial matching, fiducials may be added to the patient (e.g. by affixing) before the volume scan (e.g., via CT or MRI) is performed. The fiducials may be kept on the patient. The locations of the live physical fiducials may then be matched with those in the volume scan. The specification of the locations of the fiducials on the live patient may be performed using the tip of the navigated probe in some embodiments, and the focal point of the digital surgical microscope in other embodiments.

In landmark matching, physical landmarks on the live patient (e.g., the corners of the eyes) can be matched to corresponding landmarks in the volume scan data. Similar to fiducial location, the specification of the locations of the landmarks on the live patient may be performed using the tip of the navigated probe in some embodiments, and the focal point of the digital surgical microscope in other embodiments.

In trace, the user may be instructed by the software to use the navigated probe to trace over a uniquely shaped portion of the user anatomy (e.g., the saddle of the bridge of the nose including some of the area under the eyes). Also or alternatively, the focal point of the digital surgical microscope may be used in conjunction with robot moves about the region, with an autofocus mechanism providing a means of staying on the surface of the patient's anatomy.

Other forms of patient registration may include touchless registration using a laser, and touchless registration using photogrammetry/stereogrammetry.

At step 1130, the surgeon may review patient data and may verify the registration. If the registration is not accurate enough (e.g., does not satisfy a similarity threshold), decision step 1140 provides a logic for returning to step 1120 to repeat the registration step(s). If or after the registration is sufficiently accurate (e.g., satisfies a similarity threshold), workflow proceeds to steps 1142, which occur in most instances in the sterile realm of the operating room.

To prepare the patient and the digital surgical microscope for use in the sterile field, step 1150 includes covering the patient and the digital surgical microscope in one or more sterile drapes. Appropriate openings may be aligned as needed for the digital surgical microscope. For example a lens window may be aligned to the optics main entrance to the digital surgical microscope. The area of the patient where surgical entry is to occur may be exposed through the patient drape. The patient's skin may be sterilized with an antiseptic solution.

The earlier patient registration previously described in step 1120 may have occurred in a non-sterile field with an undraped patient and clamp as well as possibly a non-sterile navigated probe. Since the clamp was undraped and non-sterile, the patient reference navigated target may considered non-sterile. Thus, at step 1160, this target and/or the navigated probe (e.g., if used) may be replaced with sterile equivalents.

Referring to the workflow of FIG. 4, in relation to steps after 1160, the main portion of the surgery may begin. At step 1170, using the planning, incision points and/or paths may be marked or otherwise indicated on the patient. An advantage of the integrated surgical navigation and visualization system is that these incision points and/or paths can be drawn virtually as overlays over the live view as an alternative to physically marking the patient. This is quite useful since such points and/or paths may persist throughout the approach whereas physical marks are immediately removed since they are on the outermost layer of the skin which is the first to be peeled back or otherwise moved out of position (and out of visibility) during an approach.

The opening and approach may commence at step 1180 with patient incision. Some of the steps in this workflow may be specific to cranial neurosurgery but may apply to many common surgeries. At step 1180, the craniotomy begins. Another advantage of the integrated surgical navigation and visualization system may include the ability to plan the craniotomy shape in advance and draw it virtually as an overlay over the live image such that the surgeon merely needs to "cut by numbers" and follow the path with the cutting tool as drawn onscreen. This overlay persists optionally under control of the user during the whole time of the approach.

At step 1190 (e.g., as part of cranial neurosurgery) the dura may be opened. At step 1200, the digital surgical microscope head may be moved to where surgical site on patient resides. In some aspects, this step can occur earlier in the workflow shown in FIG. 4, e.g., to provide the virtual overlays for the skin incision and craniotomy steps.

At step 1210, the bulk of the surgery may be performed. More advantages of the integrated surgical system become apparent. For example, the planned trajectory may be drawn on the multiplanar reconstruction views responsive to user request. The robotic arm can be commanded under the user request to move the optical axis of the digital surgical microscope to align with the pre-planned trajectory. Also or alternatively, such alignment may be used to align the optical axis of the digital surgical microscope quasi-continuously in quasi-real-time to some vector such as the axis of a NICO port of the axis of a spinal dilator tool. Thus, the surgeon may be freed from having to manually position the microscope to keep a useful view down such axes which can change poses throughout the procedure.

Also or alternatively, at step 1210, navigated overlays may be used to allow the surgeons to "know where they are" within the patient anatomy. Furthermore, the navigated overlays may be used to allow the surgeons to have "X-ray vision" by drawing from the patient volume data portions of the patient anatomy, which might remain beneath physical structures on the patient which have not yet been removed.

When segmentation is used for example to specify the 3D shape and pose of a tumor, such a 3D shape may be drawn under user control in the correct perspective, pose, and scale to within some accuracy, and may be blended with the live image stream. This specification may allow the surgeon to identify which parts of not-yet-resected tissue might be "tumor" or "not tumor."

After the mam part of the surgery (for example a tumor resection or aneurysm clamp) is complete, the dura maybe closed and the scalp may be sutured in step 1220. The digital surgical microscope head and cart may be moved away at step 1230. The surgery may be complete at step 1240.

At step 1250, images and/or video recorded during surgery may be stored (e.g., locally, at picture archiving and communication system (PACS) 1260, at a local storage for images and/or video recorded during surgery 1270).

VII. Camera Calibration

In order to determine position and orientation information (also known as "pose" information) of a target in a navigation camera's field of view, the navigation camera may need to be calibrated. To provide accurate rendering of an object over the live field of view, the digital surgical microscope camera(s) may be calibrated.

For a monoscopic camera, the target's geometric information may also be known; a stereoscopic camera can perform absolute measurements without further input. The calibration process for monoscopic and stereoscopic cameras may, at their core, be at least nearly identical, with the stereoscopic camera requiring an additional few extra steps.

At least one high-level procedure for calibration may involve: acquiring images; solving for camera parameters; and, optionally, solving for a 3D model of the object(s) in the scene.

By adding a special calibration target in the image for each the calibration of the navigation camera and of the digital surgical microscope camera(s), the scale of the scene may be determined and two camera spaces may be tied together in a way that increases accuracy.

a. Acquire Images

In one embodiment, calibration may begin with taking a multitude (i.e., N) of snapshots (for example N=50), each with a slightly different pose of some object in the scene. The pose variation may be achieved by controlling the robot to move the digital surgical microscope head about the object to N different poses and taking a snapshot at each pose.

The snapshots (e.g., images) may be each labelled with a timestamp having a resolution fine enough to make unique the filename of each snapshot. Such identifying information can optionally be embedded in the metadata of each image.

The requirements for the object in the scene which is imaged as described above, may vary with the type of camera calibration approach used.

b. Solve for Camera Parameters

Solving for camera parameters may involve one or more approaches, such as: photogrammetry; and the traditional calibration object method.

In at least one embodiment, photogrammetry may be used to solve for camera parameters. For photogrammetry, the object can be any object that retains its shape (what we will call being "rigid") over the course of the image acquisition, and has a minimal number of algorithm-friendly "features" dispersed over the surface of the object that the algorithm can detect in a minimal number of images. However, scale of the scene cannot necessarily be determined from a random object. A scale may need to be set either manually or in an automated way by inserting a scale object in the scene.

The snapshot poses can be overlapping such that a minimal number of features can be found in more than one image, and each image can have a minimal number of such features (but not necessarily the same features across all images.) Features may be detected in each image using any of several feature detection models, such as SIFT (scale invariant feature transform.). The features detected as such can each be characterized using a feature "descriptor", which allows that same feature to be detected in multiple images and the algorithm to know that it is the same feature.

The pixel position of each such feature in the associate image can be recorded along with the feature descriptor. This pixel position may be used in camera calibration to assist in the determination of how features in the scene get projected via the camera structure to the sensor plane which converts the viewed scene into the images thus acquired.

With the assumption of the object being "rigid" over the image acquisition time, the algorithm is thus supplied with views from multiple poses of a given set of non-moving features. This may be repeated for different sets of features (typically a continually varying such set) over the set of acquired images. This information may be used to solve for the parameters in a camera model. The above described steps for acquiring images and solving for camera parameters may be referred to herein as "camera calibration" for simplicity.

A 3D model of the scene thus captured can also be calculated. Due to the ability to use any object (versus a calibration object of known structure), the scale of the world scene is not known at this point in the camera calibration using photogrammetry. Scale is set by including an object of known dimensions in at least some of the images captured during acquisition. The object can then be found manually or automatically in the 3D model and the corresponding model points The origin and axes of the calibration reference frame are set in a similar manner, for example, by including a planar object with linear orthogonal features that are used to define the X and Y axes; the Z axis is defined implicitly using the vector cross product of the X and Y axes, in a right-handed coordinate system by convention as shown in the image. An example calibration reference frame setting the origin and axes is provided in FIG. SA.

Traditional Calibration Object Method

When a calibration object of known structure Is used and the features constructing that structure can be detected by the processing algorithm, no overlapping of images may be necessary among the acquired images, and the traditional calibration object method such as OpenCV::calibrateCamera can be used. The remainder of the processing may be quite similar to that of photogrammetry.

FIG. SB is a diagram illustrating a calibration object applicable to the integrated surgical navigation and visualization system, according to an example embodiment of the present disclosure.

Using standard camera calibration methods, such as OpenCV cv::calibrateCamera, the following intrinsic camera parameters may be determined for each of the two camera eyes of the stereoscopic digital surgical microscope: principal point (ex, cy); and focal distance (fx, fy).

The cv::calibrateCamera process may be realized by taking snapshot images of a calibration target at multiple poses of the respective camera eye relative to the target which target contains computer-vision-detectable sub-objects. The sub-objects in some implementations may be unique relative to each other and thus the location of each individual sub-object relative to the whole calibration target may be known.

In some aspects, cv::calibrateCamera may use a simultaneous solving process to determine the intrinsic camera parameters as well as the extrinsic camera parameter at each pose of the camera. Said extrinsic parameters are composed of a three-dimensional translation and a three-dimensional rotation of the respective camera eye relative to a predetermined reference frame of the calibration target:

Tx, Ty, Tz (e.g., translations from the origin along each axis of the calibration reference frame); and Rx, Ry, Rz (e.g., rotations about each axis of the calibration reference frame)

The extrinsic parameters may be unique to each unique pose of the respective camera eye relative to the calibration target reference frame for each such of the multiple poses used to generate snapshot images for use in the calibration process. In contrast, the intrinsic parameters may be constrained to remain constant over all such images.

The concepts may be extensible to N-camera digital surgical microscope where N is 2 or greater.

A navigated calibration object 1300 may be created comprising a navigation target 1310 trackable by the navigation camera 200 as well as computer-vision-detectable sub-objects 1320 arranged in the reference frame of the navigation target in known positions and rotations (i.e. in known poses.)

A navigation target 210 trackable by the navigation camera may be affixed rigidly to some physical frame common to the cameras' respective optical systems. In some embodiments, one or more additional such targets may be placed variously about the frame such that the localizer (i.e. the navigation camera) can "see" at least one target at any time over a large range of poses of the digital surgical microscope head relative to the localizer.

The navigated calibration object may be placed within view of the stereoscopic digital surgical microscope.

The stereoscopic digital surgical microscope can be set to a given zoom and focus distance. Furthermore, the stereoscopic digital surgical microscope can be made to move through N poses relative to the navigated calibration object, keeping the navigated calibration object in the field of view, and recording an image for each camera eye at each pose.

Disparity in a stereoscopic digital surgical microscope may be defined for a given onscreen point or region as the number of pixels of separation between the left and right camera eyes for a given point, region or feature of the scene at the onscreen point. For example, the center of the screen may be chosen as the point at which disparity is measured, and the onscreen center of the left camera eye may be viewing a scene feature such as the bottom left corner of an irregularly shaped triangle.

It may be determined (e.g., via user input or automatically via computer vision pattern matching such as OpenCV cv::matchTemplate( )) that the same feature appears 5 pixels to the right of the onscreen center of the right camera eye. The disparity in this case may be "+5 pixels." The determination of which direction about the central axis of the screen is positive versus negative sign may be arbitrary and predetermined.

The stereoscopic digital surgical microscope can be calibrated such that, across the whole operating range of zoom and working distance, the disparity at the center of the screen for each camera eye is at or near zero pixels when the system is in "generally good focus." In some embodiments, other points on the screen may be used and/or other values of disparity.

During image acquisition at the N poses used in calibration, the view of the navigated calibration object may be optionally kept in generally good focus via robotic movement until an "in-focus" metric is optimized such as minimized disparity. The robotic movement can be controlled via a feedback loop. The feedback loop may continually monitor the measured parameter disparity and may use a measurement to drive the robot arm such that the stereoscopic digital surgical microscope moves closer to or farther from the navigated calibration object along an estimated optical axis of the microscope, thereby adjusting the measured disparity.

The navigation camera 200 (also referred to as "localizer") may continually image the navigated targets (also referred to as "tools") in its view. The navigation processor 680 may subsequently calculate the pose in some reference frame of each such tool, and may report said tool pose info to the embedded processing unit. The reference frame used may be referred to as the "localizer reference frame" and may be typically posed somewhere convenient and sensible on the localizer camera such as at the midpoint of the line joining the camera's two eyes when a stereoscopic localizer camera is used. For example, one axis of the reference frame may be aligned with said line, another axis may point orthogonally outward from the front face of the localizer camera, and a third axis may be oriented to satisfy a right-handed Cartesian coordinate system.

At each pose of the robot (and hence of the stereoscopic digital surgical microscope) where a calibration snapshot image is recorded, the tool pose info for each the navigated calibration object and the navigated target(s) on the digital surgical microscope can also recorded and indexed to the calibration snapshot image for later use.

These poses may be represented as homogeneous transformation matrices, and may be able to transform one reference frame into another. The naming of such matrices may be chosen to allow "chaining" of multiple matrices, where the final result of the multiplication of a succession of matrices may result in the transformation of the rightmost-listed reference frame into the leftmost-listed reference frame, and the inner names may need to match. This naming and representation allows for rapid on-sight verification, e.g., to ensure that the math is correct.

The transformation from space "B" to space "A" can be written "backwards" as A_T_B and pronounced, "the transformation from space B to space A is A_T_B: B to A."

Figure 9:
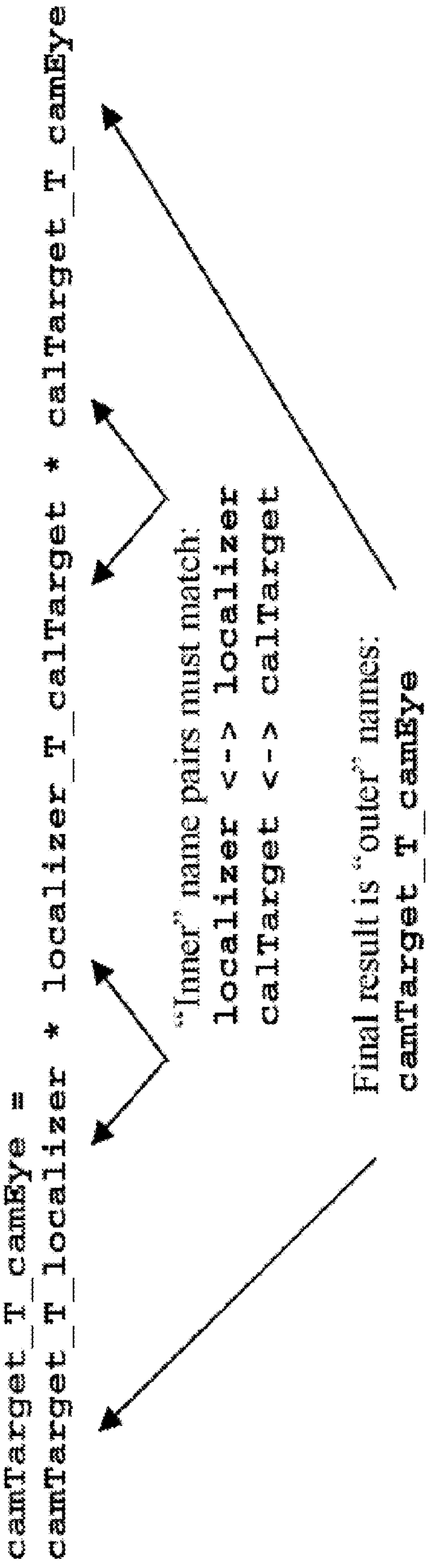
FIG. 9 is a diagram showing an example chaining of coordinate transformations, according to an example embodiment of the present disclosure.

This naming may allow easy "chaining" of transformations by lining up the "inner" pairs of space names. The final transformation may be the "outer" pair of space names, as shown in the example of FIG. 9.

The inverse of a matrix A_T_B can be written as B_T_A. For example:

$$\text{calPattern\_}T\text{\_calRefFrame} = \text{calRefFrame\_}T\text{\_calPattern.inverse( )} \quad (1.1)$$

In camera calibration, the camera may be modeled as a pinhole with a reference frame, the origin of which may be the pinhole. The camera can be placed such that the scene appears on one side of the pinhole and the sensor appears on the other side of the pinhole. For mathematical simplification, the sensor may be moved conceptually to the same side as the scene. The pinhole can be variously referred to as the "eye point", the "camera eye", or the "center of projection."

The pose of the navigated calibration object in the localizer reference frame can be denoted as:

$$\text{localizer\_}T\text{\_calTarget} \quad (2.1)$$

When multiple targets are used on the digital surgical microscope (e.g., to improve visibility over the range of possible camera poses), the poses of the multiple navigated targets on the digital surgical microscope can be reported in the same way as when a single navigated target is used. For example, a single representative pose in the localizer reference frame can be reported as:

$$\text{localizer\_}T\text{\_camTarget} \quad (2.2)$$

This reporting may not necessarily just be a notation convenience. When multiple navigated targets are used on the digital surgical microscope, one target can be chosen as the primary target and the locations of the others can be determined relative to that primary target. Thus, the navigation processor may calculate and report a single such tool pose in the tool pose information stream.

Each snapshot used in the camera calibration process may provide the pose of the camera eye relative to some predetermined reference frame of the calibration object, which typically is part of some calibration pattern used in the calibration object. Thus, the pose (i.e. the extrinsic parameters) of the camera eye can be determined relative to that calibration pattern, and may be denoted as:

$$\text{calPattern\_}T\text{\_camEye} \quad (2.3),$$

where "camEye" denotes the location and orientation (i.e. the "pose") of the reference frame of the center of projection and coordinate system of an idealized pinhole camera model of the entire optical system for a given single camera of the dual-camera stereoscopic digital surgical microscope.

For simplicity, the calibration object reference frame may be taken to be coincident with the reference frame of the navigated target mounted to the calibration object. The pose of the calibration pattern relative to the (reference frame of the) navigated target mounted to the calibration object can thus be denoted as:

$$\text{calTarget\_}T\text{\_calPattern} \quad (2.4)$$

In some embodiments, this is made to identity by making the reference frame of the calibration pattern be coincident with the reference frame of the navigation target mounted on the calibration object as in 1330.

For a given single calibration image with the associated respective camera eye poses relative to the calibration pattern, the pose of a given camera eye relative to the single representative navigated target on the digital surgical microscope may be calculated as previously described (e.g., inverse notation, matrix "chaining" method, etc.):

$$\text{camTarget\_T\_camEye camTarget\_T\_localizer} * \text{localizer\_T\_calTarget} * \text{calTarget\_T\_calPattern} * \text{calPattern\_T\_camEye} \quad \text{Eq. 3}$$

Since there may be N such calibration images and associated respective camera eye poses, there can be N occurrences of camTarget_T_camEye calculated. To reduce the effects of measurement noise and systemic error, the N occurrences of camTarget_T_camEye can be averaged to find a final camTarget_T_camEye foreach camera eye.

In some embodiments calTarget_T_calPattern can be made by design to be the identity matrix, simplifying the equation.

The Tx, Ty, Tz translations are each averaged in a linear manner.

Averaging rotations Rx, Ry, Rz can be performed, for example, by converting the angular set to quaternions, checking that none are polar opposites and solving using, for example, a Markley-type method.

After the above steps are complete, system calibration may be deemed as complete.

In a typically offline process, the patient can be scanned volumetrically resulting in a three-dimensional sampling of the relevant patient anatomy in some reference frame (e.g., a reference frame of the scanning device).

The navigated target mounted to the patient clamp may also referred to as the "patient reference target." The patient reference target plays a similar role during runtime use of the system as the navigated target mounted to the calibration object did during the calibration process.

A patient registration process can be performed, resulting in knowledge of the pose of the relevant patient anatomy relative to the patient reference target and denoted as:

$$\text{patientTarget\_}T\text{\_patientData} \quad (2.5)$$

Finding where the camera eyes are looking in the patient data

The combination of the information described above may be used to determine where each of the respective camera eyes of the stereoscopic digital surgical microscope are looking in the patient data during runtime use of the system. In modem computer graphics systems, the inverse of this construct can be calculated. Thus, the pose of the patient data in each of the respective camera eyes of the stereoscopic digital surgical microscope is determined as:

$$\text{camEye\_T\_patientData} = \text{camEye\_T\_camTarget} * \text{camTarget\_T\_localizer} * \text{localizer\_T\_patientTarget} * \text{patientTarget\_T\_patientData} \quad \text{Eq. 4}$$

The above described equation may be the "model-view" portion of setting up the computer graphics renderer; the equation describes how the model (e.g., the patient data) is to be viewed.

A projection matrix of the computer graphics system may be used to describe how points in the scene are projected onto the display screen. The camera calibration process may be similar to determining how points in the scene are projected onto the camera's image sensor. The camera intrinsics resulting from camera calibration may be used directly in creating the projection matrix.

In some computer graphics systems (e.g., OpenGL), the final projection process can also include a mapping to an interim space (e.g., the normalized device coordinate space). This can be achieved by taking the projection matrix just described and pre-multiplying by another matrix. The result can also be referred to as a projection matrix, and may offer the opportunity to directly manipulate the field of view as is described next. For simplicity, the result may be referred to as the combined projection matrix.

In association with the image sensor width and height ratio, the camera intrinsic parameters known as "focal length" may describe the angle of view of the camera and may be used directly in the projection matrix.

An optional explicit field of view calibration improves on this and may be used in some embodiments. The optional explicit field of view calibration may require an additional focus distance calibration as will be described herein.

A calibrated measurement tool such as a ruler with gradations may be placed in the scene such that its image may align with, and therefore measure, a relevant dimension of the screen (e.g., the horizontal width of the screen).

The camera may be set to some zoom and working distance setting. The ruler may be brought into focus by moving the camera head mechanically. The screen width (e.g., the horizontal field of view at the focal surface) may be read directly from the ruler.

The process may be repeated over multiple optical settings (e.g., six zooms and six working distances spanning each respective range for a total of thirty-six measurements). The results may fit to respective curves in a parameterization process as described herein, thus providing an accurate measure of the (in this example) horizontal field of view over the whole zoom and working distance range.

To assist in automating this process, a pattern may be used as the measurement tool. The pattern can be detected and measured by computer vision processes. For example, a flat plate can be adorned with a mostly symmetric checkerboard image. The dimensions of each feature of the checkerboard image may be known by design and/or measurement. Some asymmetry or other feature may be added to assist the computer vision processes as well as robot control such that the plate can be kept centered nominally in the camera view.

Multiple patterns of varying sizes may be optionally used to provide accurate calibration over a wide zoom range.

Traditional camera calibration can also provide a measure of the optical distortion of the system at the optical parameter settings at which the calibration process was performed. A set of distortion coefficients can be found and can be used in some embodiments to correct such optical distortion. In some embodiments, such distortion correction can be used to improve the field of view calibration method. Furthermore, in some embodiments, such distortion correction can be used to improve the accuracy of the overlay (e.g., how it matches the live view.)

In embodiments where an explicit field of view calibration process may be used to improve on the field of view determination for the projection matrix of the computer graphics renderer, the distance to the focal surface of each camera eye of the stereoscopic digital surgical microscope may be required to be calculated. The determination of this distance for each camera eye will be discussed herein, in relation to FIG. 7C.

Figure 6:
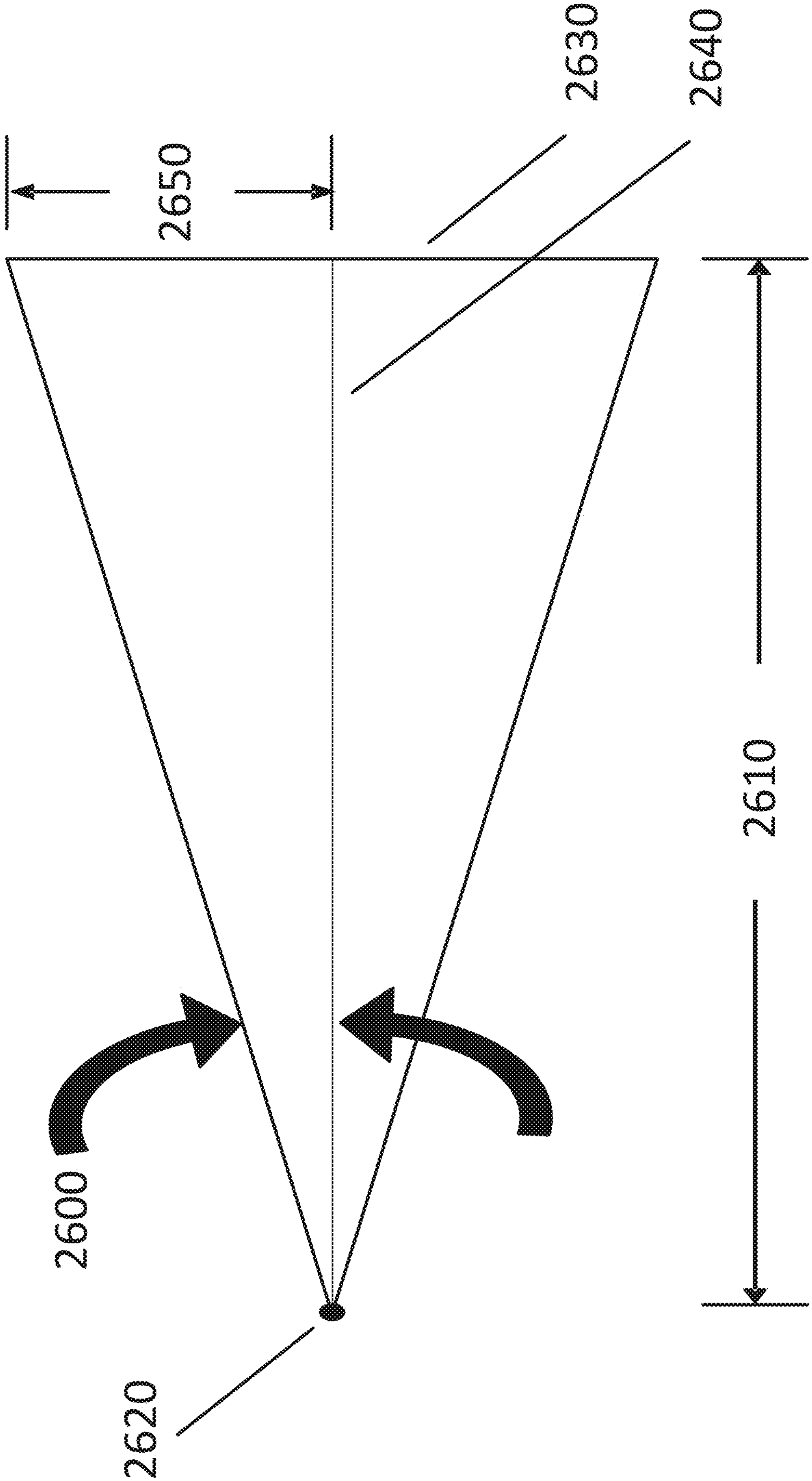
FIG. 6 is a diagram showing an angle of view applicable to the integrated surgical navigation and visualization system, according to an example embodiment of the present disclosure.

FIG. 6 is a diagram showing an angle of view applicable to the integrated surgical navigation and visualization system, according to an example embodiment of the present disclosure. With the focus distance, the angle of view can be calculated. This angle may be needed to calculate terms in the projection matrix and can be found by trigonometry, as shown in FIG. 6:

For example, the half angle 2600 can be found by measuring the focus distance 2610 from the camera center of projection (also referred to as the camera "eye point") 2620 to the focus surface 2630 along the optical axis 2640. The additional field of view calibration can provide a measure of the field of view (for example the horizontal width) at the focus surface. The half of such distance is shown as marker 2650. The tangent of half angle 2600 is distance 2650 divided by distance 2640. The inverse tangent function can then be used to calculate the "half field of view angle." The half field of view angle can be used to calculate directly certain matrix elements of the combined projection matrix as:

Matrix element (0,0)=1.0/tan (halfHorizontalFieldOfViewAngle), and

Matrix element (1,1)=1.0/tan (haltVerticalFieldOfViewAngle), where it should be noted that the horizontal and vertical field of view are related by the width and height ratio of the sensor (or equivalently of the images used in camera calibration.)

The previously described camEye_T_patientData in combination with the projection matrix utilizing camera intrinsics information determined earlier provide a faithful rendering of a duplicate representation from the (typically volumetric) patient data of any part of the relevant patient anatomy of the live patient that is within the field of view and depth of focus of the digital surgical microscope. Further, this rendering is effective in each respective eye of the digital surgical microscope, thereby enabling stereoscopic rendering of such a representation.

The rendering may be registered to the live patient view on the stereoscopic digital surgical microscope in the correct position, orientation and scale to within some tolerance of each. Further, the perspective of the render in three dimensions also matches the live view to within some tolerance.

These features along with appropriate user interface controls enable the user to "look inside" the patient even without making any incision. These features similarly allow the user to "look ahead" of where they currently are if for example they have made incisions and are performing a surgical approach to a pathology en route to providing therapy for said pathology.

Further, these features allow each of these capabilities to be viewed by the user in stereoscopic, which may greatly enhance spatial awareness and is more intuitive.

Further, these features allow the utilization of (typically volumetric) patient data on the same display as the live surgical site view, thereby reducing cognitive load of having to remember complex three-dimensional views when transitioning between the navigation device and the surgical visualization device. The presently described integrated surgical navigation and visualization system incorporates both devices, integrating them into a greater whole.

IX. Finding the Digital Surgical Microscope Camera Reference Frame

During camera calibration, the digital surgical microscope camera reference frame may be defined with its origin at the "pinhole" of the pinhole camera model. This location may also be referred to as the "center of projection" of the camera. Knowing the pose of the reference frame of the digital surgical microscope camera(s) optical center(s) relative to the reference frame of the navigation device may be significant in being able to solve for the pose of the digital surgical microscope relative to the patient data, which is the main objective of surgical navigation.

When such a pose is known to a good degree of accuracy and the camera optical parameters are modeled sufficiently well, the highest level of surgical navigation described herein can be provided. Systems and methods described herein disclose that highest level of surgical navigation.

One of the essential functions provided by the navigation is to answer the questions, "Where am I, where am I going, what is nearby?" This may be equivalent to determining the pose of the digital surgical microscope camera(s) relative to the patient data (while also knowing the camera intrinsic parameters.) This section focuses on determining the extrinsic relation between the camera and the patient data, that is, the pose between the two.

The mathematics required to calculate the pose between the digital surgical microscope (DSM) camera(s) and the patient data use 4×4 homogeneous transformation matrices to calculate the relative pose between a given pair reference frames and, for the overall system, through a chain of such reference frames. In this document, the terms "transformation", "transformation matrix", "4×4 homogeneous transformation matrix", "matrix", "pose" and "relative position and orientation" are used interchangeably.

The terminology used here for such 4×4 homogeneous transformation matrices 1s: A 4×4 homogeneous transformation matrix that takes points in reference frame A and transforms them to reference frame B is written as B_T_A and is read "backwards" such that it is pronounced "A to B."

For example the matrix dsmCam_T_patientData is read "backwards" as "patient data to DSM camera" (when the abbreviations are said in full) and thus a point in patient data space can be pre-multiplied by this matrix to give the location of the same point in DSM camera space:

PIDSM=dsmCam_*T*_patientData**P*|PATIENT DATA

It should also be noted that a 4×4 homogeneous transformation matrix from reference frame A to reference frame Bis the matrix inverse of the transformation from reference frame B to reference frame A, and vice versa. Thus:

dsmCam_*T*_patientData=patientData_*T*_dsmCam.inverse( ) and patientData_*T*_dsmCam=dsmCam_*T*_patientData.inverse( )

To transform from one reference frame to another it is possible to transform through intermediate reference frames, similar to there being multiple different routes between two physical locations. This is written for example as follows:

dsmCam_*T*_navCam=dsmCam_*T*_navTarget*navTarget_*T*_navCam which says, "The transformation from the navCamreference frame to the dsmCamreference frame (left-hand side of the equation) equals the transformation from the navCam reference frame to the navTarget reference frame premultiplied by the transformation from the navTargetreference frame to the dsmCamreference frame.

Note how the inner names (navTarget) match up on the right-hand side of the equation, and the outermost names (dsmCamand navCam) are the final result on the left hand side, m the order they appear on the right-hand side. That's key and that's why we write the transformation name "backwards."

Writing them that way makes it so much easier to write and read the equation and know that it's what we need. The chain can be extended indefinitely as long as the inner names match up, such as in:

FT_A=F_T_E*E_T_D*D_T_C*C_T_B*B_T_A a. On-Head Navigation Camera Math

Figure 7A:
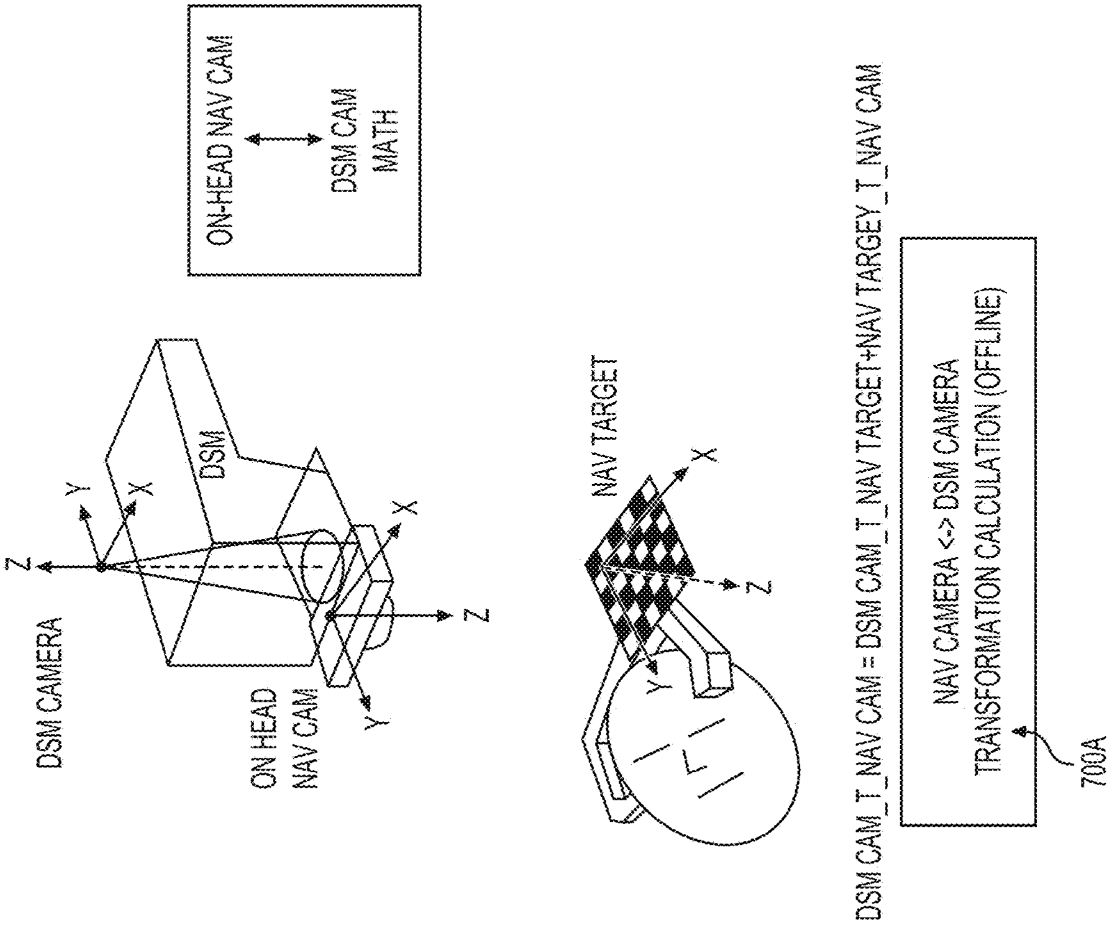
FIG. 7 is a flow diagram showing an example method for a focal reference frame calibration applicable to the integrated surgical navigation and visualization system, according to an example embodiment of the present disclosure.

To determine the relative pose between the digital surgical microscope camera(s) and the patient data, the on-head navigation camera method may involve:

(1) An (optionally offline) determination of the relative pose between the digital surgical microscope camera(s) and the navigation camera. This is referred to here as "camera registration." An example schematic model and calculation of the relative pose between the digital surgical microscope camera and the navigation camera is shown in FIG. 7A (2) A peri-operative determination of the relative pose between the patient data and the navigation target. This may be referred to herein as "patient registration" for simplicity.

Figure 7B:
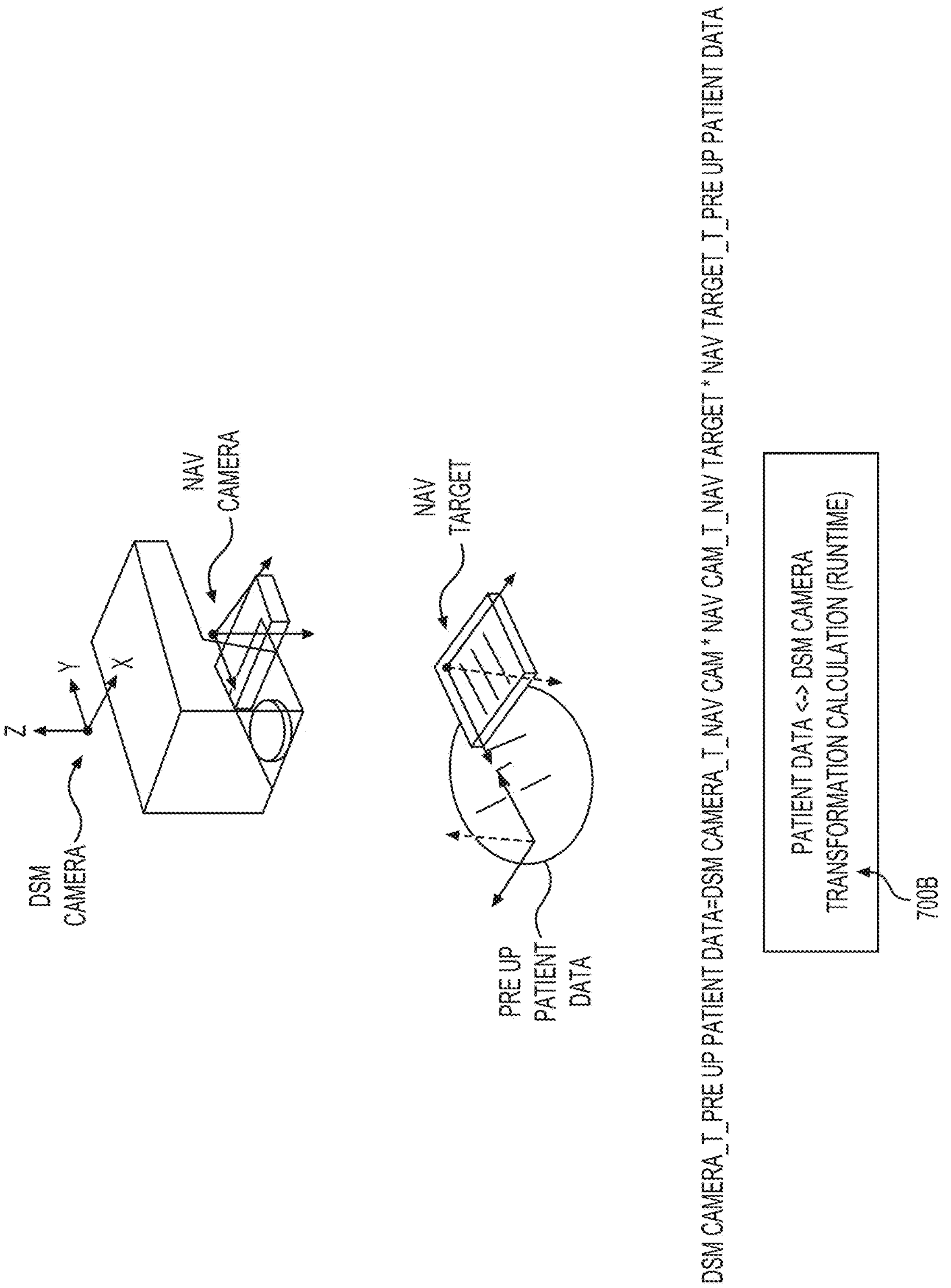

(3) A runtime determination of the relative pose between a navigation target in the scene affixed rigidly to the patient (typically via bony structures directly or indirectly). An example schematic model and calculation of the relative pose between the navigation target in the scene on the patient is shown in FIG. 7B As shown in FIG. 7A, the calculation of the relative pose between the digital surgical microscope camera and the navigation camera may involve offline step 700A, indicated as Navigation camera <-> DSM camera transformation calculation (offline). Step 700A is the camera registration step and determines the relative pose between the digital surgical microscope camera(s) and the navigation camera. Step 700A of Navigation camera <-> DSM camera transformation calculation (offline) may be calculated as:

dsmCam_*T*_navCam=dsmCam_*T*_navTarget*navTarget_*T*_navCam, where dsmCam_T_navCam is the camera registration result describing the location of the reference frame of the digital surgical microscope camera(s) relative to the reference frame of the navigation camera; dsmCam_T_navTarget is the pose of the digital surgical microscope camera(s) relative to the navigation target and is determined during camera registration via camera calibration and/or photogrammetry; and navTarget_T_navCam is the pose of the navigation target as seen by the navigation camera and is solved per frame using an algorithm such as OpenCV::findChessboard-Comers to find critical features of the navigation target in every frame (or a subset of frames, depending on available compute capability) in concert with OpenCV::solvePnP to take those image locations and along with the navigation camera calibration information determine the pose information of the navigation target.

As shown in FIG. 7B, the calculation of the relative pose between the navigation target in the scene on the patient may involve step 700B, indicated as "Patient data <-> DSM camera transformation calculation (runtime)." Step 700B refers to the calculation of the relative pose between the digital surgical microscope camera(s) and the patient data and may be a final single matrix result needed to render a representation of the patient data from the same orientation and position that the digital surgical microscope camera(s) are relative to the live patient. This enables augmented reality for surgery.

For the stereoscopic digital surgical microscope camera, a further more transformation is found and used in the equation to account for camera eye separation. To render optionally other regions of the patient data (for example a slice deeper than we are currently looking,) an additional simple transformation, such as a translation along the Z axis, is found and used in the equation.

Thus, step 700B, "Patient data <-> DSM camera transformation calculation (runtime)," may be performed via the following transformations:

$$\text{dsmCam\_T\_patientData} = \text{dsmCam\_T\_navCam} * \text{navCam\_T\_navTarget} * \text{navTarget\_T\_patientData}$$

where dsmCam_T_patientDatais the final single matrix needed to render the patient data as just described; dsmCam_T_navCamis the "navigation camera to DSM camera" transformation and is found via the camera registration step described elsewhere in this document; navCam_T_navTargetis the pose of the navigation target as seen by the navigation camera as described elsewhere in this document; and navTarget_T_patientDatais the transformation output describing the patient anatomy pose relative to the navigation target and is determined during the patient registration step described elsewhere in this document.

b. Legacy Navigation Camera Math

The methods required to calculate the pose of the digital surgical microscope camera(s) in systems and methods disclosed herein are an improvement over legacy mathematical methods used in the legacy real-time application at least because the improved methods disclosed herein uses fewer terms. Each term adds to inaccuracy. The methods disclosed in this present disclosure has only three terms on the right-hand side. The legacy math has four terms on the right-hand side:

$$\text{dsmCam\_T\_patientData} = \text{dsmCam\_T\_dsmTarget} * \text{dsmTarget\_T\_localizer} * \text{localizer\_T\_patientRefFrm} * \text{patientRefFrm\_T\_patientData}$$

where dsmCam_T_patientDatais the final single matrix needed to render the patient data as previously described; dsmCam_T_dsmTargetis the transformation from the IR target mounted on the digital surgical microscope head to the digital surgical microscope camera(s) and is found using a navigate calibration plate and process as described elsewhere in this present disclosure; dsmTarget_T_localizer is the inverse oflocalizer_T_dsmTargetwhich is the pose of the on-microscope-head IR target in the navigation localizer camera space; localizer_T_patientReffrm is the pose of the patient reference frame IR target (for example mounted on the clamp) in the navigation localizer camera space; patientRefFrm_T_patientDatais the transformation output describing the patient anatomy pose relative to the navigation target mounted on the clamp (or similar) holding the patient anatomy in place and is determined during the patient registration step described elsewhere in this present disclosure.

X. Accuracy Improvement a. Improving Accuracy by Reducing the Number of Devices in the System The navigation device may be integrated into the microscope head and thus can move rigidly with the head. Therefore no target may be needed to determine the movement of the head. This may reduce the number of devices in the navigation calculation path and thus improves accuracy by removing the inaccuracies introduced by those extra devices.

For example FIG. 1A, which shows an example legacy surgical navigation system is based on three devices: an optical microscope with an infrared target ("antlers"), a remote localizer, and a patient reference frame (3 devices). In contrast, FIG. 1B, which shown an auto-navigating, integrated surgical navigation and visualization system comprises only two devices, a digital surgical microscope extended with navigation device, and a patient reference frame.

The math required to calculate the real-time pose of the digital surgical microscope camera(s) relative to the patient data shows why there is an accuracy improvement over the legacy solution application: There is one fewer term in the matrix multiplication. This means that the inaccuracy presented by the physical or virtual mechanism that that term describes, is removed. This decreases inaccuracy which is to say it increases accuracy or alternatively it improves accuracy.

b. Improving Accuracy by Greatly Reducing Time Between Calibration and Procedure Additionally the methods discussed in the present disclosure to calibrate the navigation camera, calibrate the digital surgical microscope camera(s), and calculate dsmCam T navCam can be performed at the time of the procedure, thereby eliminating inaccuracy that can creep in over the time elapsed preceding the procedure since the latest in-service calibration of a legacy navigation device.

It should be noted however that the autonavigating, integrated surgical navigation and visualization system also allows such calibrations and calculation at in-service time if desired, instead of at the time of procedure. This saves some computation time during system setup at the time of the procedure.

c. Patient Registration

The registration step performs the calculation of patientRefFrm_T_patientData. The patient preop data is ingested and managed, the patient is prepared and the cal/navigation targets applied and scanned for surface data which is then aligned to the preop data.

d. Patient Scan Data

1. Data Ingestion and Reconstruction

The data from the patient scan(s) are ingested into the system and in the case of 3D data placed in a data format convenient for 2D rendering as well as 3D (volumetric) rendering of the data.

11. Surface Extraction from 3D Scan Data

A surface generally corresponding to the patient's skin is extracted from the 3D scan data. This surface is used to align to the similar surface extracted from the live patient data.

111. Registration of Different Modalities

Different modalities such as CT and MRI are used for generating patient scan data. The registration described thus far aligns the data from the live patient scan and the data from one modality scan (typically CT.) To use an additional modality, that modality may need to also be registered to the live patient data. The registration step includes optionally use of a modality alignment module which aligns other modalities either directly to the live patient data or by registering to the already-aligned modality.

e. Patient Preparation

Patient positioning and clamping (which can be described as "fixing in place") proceeds as in legacy surgical navigation, typically after the patient is anesthetized. The patient is positioned appropriately for the procedure and the relevant anatomy fixed in place as much as possible. Then cal/navigation target(s) are affixed to the patient anatomy, typically to bony structures via a clamp attached to such structures (such as in the case of cranial surgery, to the clamp such as a Mayfield clamp that holds the patient's skull in place or as in the case of spine surgery to a patient's vertebra.)

f. Peri-Operative Scan of Live Patient Data

After patient preparation, the digital surgical microscope camera(s) and navigation camera(s) are used to gather live patient data to enable patient registration and navigation.

g. Image Acquisition

The surface of the live patient is captured by moving the robot about the patient in many poses taking a snapshot at each pose while keeping the relevant part of the patient's anatomy in the field of view of the digital surgical microscope camera(s) for each snapshot. Keeping the patient's anatomy in the field of view is achieved via one of the following means, or a combination of some or all of them:

- Manual "driving" the robot around the acquisition space by an operator around during image acquisition
- Using the software to instruct an operator to position and orient the microscope approximately in a known starting configuration relative to the patient (and appropriate for the patient position and procedure), and then controlling the robot via the software to move through pre-defined paths that are prescribed previously to capture the relevant anatomy of a very large percentage of patients over a spherical range
- Calculating a center point of a sphere and moving the microscope head about that sphere while keeping the focal point of the microscope coincident with the center of the sphere to within some tolerance (e.g. the tolerance of "lock-to-target")
- Using deep learning to extract patient anatomy features from images captured during acquisition and controlling the robot position and orientation to achieve sufficient coverage h. Calibration Target(s)

One or more calibration targets are mounted rigidly to the patient anatomy typically indirectly by mounting on a clamp for example. This calibration target may need to appear in at least a small number of the snapshots. Calibration targets are optionally used as navigation targets as well.

1. Photogrammetry

The images captured during patient registration image acquisition are sent to a photogrammetry module which performs the following, typically in this or a similar order, but some steps can be performed in a different order or in parallel with other steps:

- Feature detection in each image using a feature description mechanism such as SIFT
- Correlation of features in images taken from "nearby" poses of the microscope head relative to the patient during image acquisition. This is a relatively sparse set of points compared to the number of pixels in an image.
  - An alternative solution is to use the calibrated stereoscopic digital surgical microscope camera to extract a surface point per matched stereo pixel pair which is a much more dense dataset; the surface thus extracted per stereo snapshot taken at one pose is later stitched into a single larger whole with surfaces extracted from stereo snapshots taken at other poses.
- Solver-based solution to a camera extrinsic model for each image in the acquisition
- Optionally at this time: Solver-based solution to a single camera intrinsic model unified over all images
  - The requirement for this to work well is to keep the digital surgical microscope camera(s) at constant zoom and working distance settings for the entirety of the image acquisition
  - This step can be done optionally offline at some time (even days, weeks, months, years) before the procedure
- Scale and reference frame origin and orientation specification.
  - Scale is found via readily detected features of known dimension such as two April tags placed a known distance away from each other
  - Reference frame origin and orientation is found via the calibration target(s); a directional set of features along two orthogonal lines enable determination of two axes; the third axis is determined using the cross-product of the first two in a right-handed coordinate system (a left-handed coordinate system could be used instead)
  - The patient reference frame origin and orientation is specified to be coincident with the reference frame just found
  - If a navigation target is used that is different from the cal target, then enough features present in both may be required to be captured by either the digital surgical microscope camera(s) or the navigation camera (if we are re-calibrating the navigation camera at this time) such that the transformation between the two reference frames (cal and navigation target) can be calculated from the photogrammetry result.
- Patient anatomy 3D model generation for the relatively sparse set of data represented by the feature extraction step. This is the surface extraction step for the live patient data
  - When the stereoscopic pixel matching approach is used, model generation is significantly more accurate
  - For the sparse model a subsequent step of "densifying" the model mesh is taken
- Data export to the main application including camera calibration information and patient anatomy 3D model.
- This procedure proceeds in the same manner for each the left and right eyes of the stereoscopic digital surgical microscope with an additional eye separation value added in optionally
- This procedure is performed at a single zoom and working distance setting for example at a mid-range zoom setting. To function over the full range of zoom and working distance one of two methods are used:
  - The "brute force" method in which the zoom and working distance space is divided into a finite number of value combinations and a calibration performed at each possible value combination. The digital surgical microscope optics are then constrained to operate at those values only
  - The "calculate and interpolate" method in which a single zoom is selected (for example a mid-range zoom value) and the calibration is repeated for a sampling of working distances over the working distance range. These are interpolated for intermediate working distances. The zoom value is incorporated by changing the field of view (essentially scaling the image) about the principal point of the camera. The amount of scale is determined by a separate calibration step which maps field of view to zoom motor counts.

Note that the navigation camera is also optionally imaging at this time such that it can be re-calibrated and/or the matrix dsmCam_T_navCam can be (re)calculated at this time very close to the procedure instead of days, weeks, months, years in the past, over which time the calibration and/or calculation may have degraded.

J. Using the Probe for Registration

As in legacy navigation, using a navigated probe to trace the surface of the patient is an optional means for extracting the patient surface for the purpose of registration. The tip of the probe relative to a probe-mounted navigation target is found during a calibration and verification step explained elsewhere, and the tip is tracked during a specific "trace" time and over a predetermined general region of interest on the patient as indicated to the user by the software.

The location of the probe as reported by the navigation module may be sampled at a rate sufficient to sample the surface path at a resolution high enough for surface feature extraction.

k. Aligning the Surfaces

In this step all or some of the captured portion of the surface of the live patient data is matched (also known as registered, or aligned) to all or some of the captured portion of the surface of the patient in preop data. This process results in the transformation patientRefFrm_T_patientData.

The two surfaces do not typically share a common coordinate system, nor is this feasible. Thus the transformation between the two coordinate systems may be determined.

Determining the transformation between the two coordinate systems is achieved by first optionally maneuvering the respective renderings of each dataset to be "close by each other" using a software visualization module. Any transformations used during this operation are recorded and become part of the final transformation.

The next step is to use one of several well-known alignment algorithms and/or techniques such as "iterative closest point" (ICP) which calculates a transformation between the two datasets that is best in some error minimization sense.

The transformation search algorithm is typically constrained to search for just translation and rotation and ignore scale, but due to differences in the calibration of the various devices involved in generating the two datasets, a search over a small range of scale is sometimes useful.

The output is a transformation matrix that describes the pose of the patient data relative to the cal target. If a navigation target is used that is different from the cal target, the pose between the two targets is included in calculating this output.

Thus when the rest of the system is enabled to determine the position and orientation of the digital surgical microscope camera(s) relative to the navigation target(s), and the camera intrinsic parameters are known for its current zoom and working distance, the system is enabled to render a view of the patient data over the live view of the patient. This is augmented reality for surgery.

1. Intraoperative Patient Data Updates

The same process of patient scan data registration to the live patient pose relative to the navigation target(s) is used to register new or updated data such as intraoperative MRI that might be generated during the procedure.

m. Navigation

Following the previously-described setup steps, the system is ready to provide surgical navigation to the user. The auto-navigating digital surgical microscope is placed to enable the navigation device to view the navigation target or targets XX mounted rigidly to the patient anatomy and to enable the digital surgical microscope camera(s) to view the areas of the patient anatomy relevant to the procedure. The navigation device data output is communicated to the main information processor module either in raw or processed form. If raw, then the processing is performed in the main information processor module. The data of interest is the value of the transformation navCam_T_navTarget with real-time or near real-time updates.

With this input as well as input from the digital surgical microscope camera(s) about the current zoom and working distance settings of said camera(s) in addition to the information described previously needed in the runtime math, the system is enabled to provide augmented reality for surgery.

n. Tool Usage

Navigated tools are an important part of the surgeon's toolbox. The navigated probe is the most commonly used such tool, and it consists typically of a dully-pointed metal rod to which is affixed a navigation target that can be detected by the navigation camera. It is used to make quick determinations of "what is where".

A calibration step is used to determine the probe tip location relative to the probe's navigation target; this step often performs the function of a verification step as well: after the first calibration, the system can simply recognize the tool's' target and verify that its tip is where the system thinks it should be to within a tolerance. The microscope is typically not used when the probe is being used, at least not immediately concurrently.

o. Positioning the Microscope for Tool Usage

The navigation camera may need to be able at all times to view the tool's navigation target(s). In the case where the surgeon does not need the microscope during probing, the user selects a preset position for the robotic arm which positions the microscope head out of the surgical field but close enough and in an orientation such that the navigation camera can still view the navigation target(s) on the tool as well as the one(s) affixed to the patient anatomy.

DSM robotic arm and head may move off to the side of the surgical field, tilted such that the navigation camera can still view all the necessary navigation target(s)

p. Calibrating the Tool

Calibrating the tool (sometimes referred to as verifying the tool) is the task of locating the tooltip relative to the tool's navigation target. This is achieved by providing a known location relative to a navigation target (or calibration target) and instructing the user to place the tooltip at that known location. The navigation device is constantly updating the pose of each target it sees in the scene and thus the translational component of the relative pose between the targets represents the tooltip offset from its navigation target.

To facilitate tooltip placement, the "known location" is made to be the bottom of a physical "divot" into which the tooltip can fit and be kept in nominally the same location while allowing the tool to be pivoted about its tip. The software instructs the user to indicate when the user has the tooltip in place in the divot, for example by requiring the manual click of a button.

An improvement to the manual-click method is to continually monitor in the software the translational offset magnitude between the tool navigation target and the target used for verification. If the magnitude stays unchanged within some tolerance for a given amount of time during the verification process, it can be presumed that the user is holding the tip in the "divot." However, the pose of a tool at rest outside the divot also has an unchanging translational magnitude relative to the calibration target.

As a further improvement to this process, the user is instructed to pivot the tool (and thus its navigation target) through some range of angles while keeping the tooltip placed in the "divot"; this causes change of angles in the relative pose while the magnitude of the translation remains relatively unchanged. This is a more robust way of determining whether the user is trying to verify the tool.

The procedure just described provides only translational offset of the tooltip from the tool navigation target. If tool orientation is important to know then a structure is provided which enforces tool navigation target orientation relative to the verification device navigation target.

This data can be stored in the tool definition file for later tool use without the tool calibration step, but as a tool can be deformed through use or handling, the verification step is generally required before the start of each use, for example at the start of a procedure. The user can optionally re-verify the tool at any time during the procedure.

q. Camera as Probe

As the steps in this document describe, the location and orientation of the digital surgical microscope camera(s) are known relative to the patient data. This means that the microscope can optionally be used to provide the same exact function as the navigation probe: to show in the navigation data "where am Ilooking?"

r. Augmented Reality for Surgery

With surgical navigation enabled as described, the system is ready to provide augmented reality for surgery at all of the levels of surgical navigation complexity mentioned previously. The mechanism for presenting such augmentation varies per procedure, surgeon preference, data availability and quality, and registration results.

s. Patient Data on System Displays

The patient data is displayed based on surgeon preference in various manners:

- Sharing the main visualization display with the live view of the surgical site.
- On its own display near the surgeon's field of view
- Overlaid onto the live view of the surgical site, with options for the user to specify on/off and opacity The augmentation shown and the methods used in those data representations include but are not limited to:

i. Tip and Vector in Data

When a "Display tip and vector" option is selected in the software, the tip of each calibrated and verified tool (including the digital surgical microscope camera(s)) in view of the navigation camera is represented in the patient space by a uniquely colored annotation such as a dot. A glossary is optionally included to "connect the dots" as it were to the type of tool.

Alternatively a small text annotation is drawn near the dot and provides relevant information about the tool. The line along which lies the main linear feature of the tool (for example the optical axis of the digital surgical microscope camera(s)) is optionally drawn as well, with one end at the tip.

ii. Tool Orientation

For certain tools, the tool orientation is known relative to the navigation target. This enables drawing in the patient data an annotation incorporating the orientation as well as drawing the data oriented onscreen to how the tool is "seeing" the patient anatomy. For the digital surgical microscope, this orientation is made to correspond with the live view, reducing the complexity required for the surgeon to gain a mental picture answering the question, "where am I?" This reduces the surgeon's mental load during navigation use.

iii. Path Projection

The line along which lies the main linear feature of the tool is optionally extended ahead of the current tooltip to envision the path ahead for the tool. For example when inserting a pedicle screw during spine surgery, the current location of the screwtip is shown as well as its projected path as it is inserted further. This is critical information necessary to ensure that the screw is fully captured by the pedicle and does not break through into, for example the spinal cord column.

iv. Overlay

Since the optical parameters of the digital surgical microscope camera(s) are found during calibration and the pose relative to the patient data is known, an (optionally stereoscopic) 3D rendering of the patient data is rendered optionally over the live view.

Additionally, the parameters used to select the data to be rendered can be controlled to optimize the value to the surgeon. For example, a pre-planned approach corridor can be rendered in (optionally stereoscopic) 3D such that only the currently visible part of the approach plus the next few millimeters are shown. As another example, a 2D slice can be rendered at various levels along the optical axis relative to the focal point such that the surgeon can have a clear look at what is inside the patient.

This adds high value to the auto-navigating, integrated surgical navigation and visualization system described herein; it is essentially "x-ray" vision, enabling the surgeon to see into the patient even where no incision exists or where the surgeon has not yet exposed.

XI. Calibrating the Pose of a Visually Relevant Reference Frame Relative to the Representative Navigated Target on the Digital Surgical Microscope A separate calibration may be performed to determine the pose of a visually relevant reference frame relative to the representative navigated target on the digital surgical microscope. For example, this visually relevant reference frame may be the screen center for each eye of the stereoscopic digital surgical microscope.

The calibration may be performed by setting the microscope optical parameters such that the respective image captured by each camera eye is at or near optimal optical focus at said screen center. The optics may be designed and tuned such that at a given working distance setting the optics are focused on a point in space some distance away from the microscope.

Further, the optics may be designed and tuned such that the screen centers of the eyes of the stereoscopic digital surgical microscope are imaging the same point in space to within some tolerance when "in focus" at a given set of microscope optical parameters.

The point in the scene which is projected to the respective screen centers of each camera eye is referred to as the "focal point" of the microscope. Thus this separate calibration in part determines the location of the focal point of the camera relative to the representative navigated target on the digital surgical microscope.

There may be a focal surface to which can be assigned an ongm and coordinate system to define a "focal reference frame." This may redefine a focal point as well as "up" and "right" vectors which may allow the orientation of the camera image(s) onscreen.

While physically the focal surface might not be purely planar (e.g., it may be slightly curved), the focal surface may be taken to be a two-dimensional plane for simplicity and ease of explanation. The origin of the focal reference frame may be taken in some embodiments to be the location in screen center of the calibrated camera and the pose of the focal reference frame is such that it is oriented orthogonally to the optical axis at a given optical setting of the microscope with its X axis pointing along the horizontal direction of the image sensor proceeding positively to the right and its Y axis pointing along the vertical direction of the image sensor proceeding positively downward. In practice, there might be additional "flips" of axis direction and offsets of the origin location to conform with preferred graphics systems, system requirements, user preference and the like.

Thus this separate calibration may determine the pose of the microscope's "focal reference frame" relative to the representative navigated target on the digital surgical microscope.

Since the focal point of the stereoscopic digital surgical microscope may be made to be the same for each of its component single cameras (i.e. each "eye"), and the onscreen axes may be coincident or nearly so, there may not be a need to perform a separate focal reference frame calibration per eye. In such embodiments, there may only be one calibration performed for the stereoscopic digital surgical microscope as a whole.

Figure 7C:
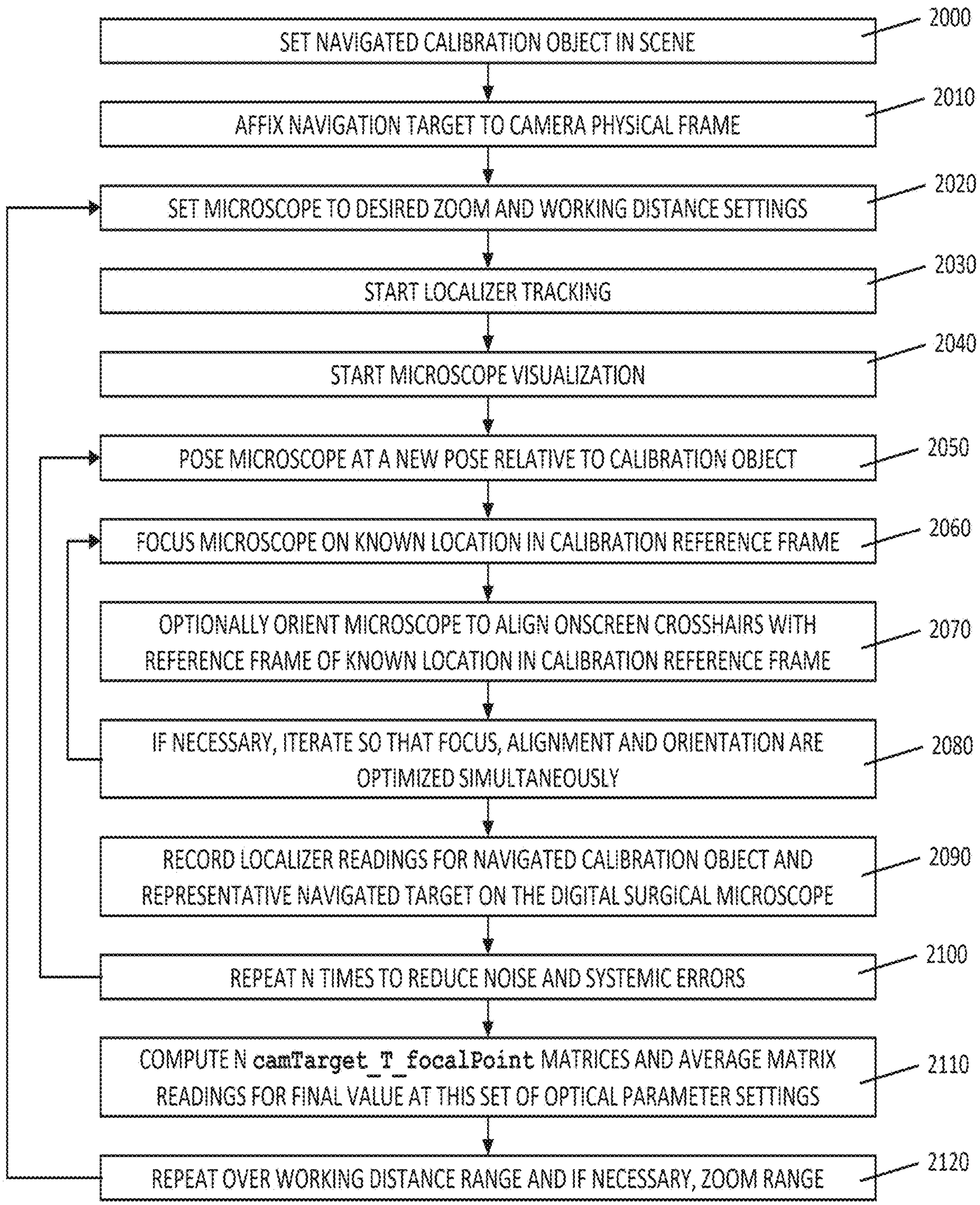

FIG. 7C is a flow diagram showing an example method for a focal reference frame calibration applicable to the integrated surgical navigation and visualization system, according to an example embodiment of the present disclosure.

At step 2000, a navigated calibration object can be set into the scene. The calibration object may include one or more structures, (e.g., a crosshair) to aid alignment of the visually relevant reference frame of the microscope to the reference frame of the navigated calibration object (e.g., via a crosshair or other alignment aid on the navigated calibration object). Also or alternatively, the onscreen center and axes may be drawn onscreen by the graphics module to aid the operator in aligning the onscreen center to the calibration object alignment structure(s).

At step 2010, the navigation target may be affixed to the camera physical The microscope may be set to a desired zoom magnification and working distance settings at step 2020. The localizer tracking may be started at step 2030. The localizer may detect the presence of, and determine the pose in localizer space of, each trackable navigation target in its viewable scene. In some aspects, those targets may comprise the navigated calibration object and the representative navigated target on the digital surgical microscope.

At step 2040, microscope visualization can be started. At step 2050, the microscope can be posed relative to the navigated calibration target (or vice-versa.)

At 2060, the microscope can be focused on the calibration object alignment structure. For example, this structure may comprise a crosshair. To simplify and reduce error in the matrix calculations, the crosshair may be located at the origin of the calibration object's navigated target, and its X and Y axes may be coincident to those respectively of said target. The crosshair may be two-dimensional; the imagined Z axis may also taken to be coincident to the corresponding axis of the calibration object's navigated target.

At step 2070, the microscope may be optionally oriented to align the onscreen crosshairs with those of the calibration target. This step may be optional, for example, if the focal reference frame provides more information than is needed. In some embodiments, it may be sufficient to determine only the focal point location relative to the representative navigated target on the digital surgical microscope and to not also determine the orientation of the whole focal reference frame relative to said target.

Since changing the orientation of the microscope could change its optimal focus point, an iteration may be performed at step 2080 if appropriate to optimize the focus as well as the relative location (i.e. alignment) and orientation of the onscreen crosshairs to the calibration target crosshairs.

The localizer readings localizer_T_camTarget and localizer_T_calTarget may be recorded at step 2090. As noise reduction and systemic error reduction practices, it may be desirable to repeat, at step 2100, the overall measurement at a number (for example N=25) of different poses of the microscope relative to the navigated calibration target.

At step 2110, the function camTarget_T_focalRefFrame can be solved as:

$$\text{camTarget\_T\_focalRefFrame} = \text{camTarget\_T\_localizer} * \text{localizer\_T\_calTarget} * \text{calTarget\_T\_focalRefFrame},$$

where calTarget_T_focalRefFrame in some embodiments is identity by design to simplify and reduce errors in matrix multiplication. The simplified equation thus becomes:

$$\text{camTarget\_T\_focalRefFrame} = \text{camTarget\_T localizer} * \text{localizer\_T\_focalRefFrame}$$

These N solutions may be averaged using matrix averaging as described elsewhere in this document to determine a final value for camTarget_T_focalRefFrame.

For a more complete calibration, this process may be repeated at step 2120 at a number of zoom and working distance settings across the operating range of each such parameter. A curve may be fit for each relevant output parameter set as a function of input parameters. This process may be referred to as parameterization. The output parameter set may be the focal point pose relative to the representative navigated target on the digital surgical microscope. The input parameters may include zoom and working distance settings from the camera control module.

Using the previously described camTarget_T_camEye and camTarget_T_focalRefFrame functions, the focal point reference frame pose relative to each respective camera eye of the stereoscopic digital surgical microscope can be determined by:

$$\text{camEye\_T\_focalRefFrame} = \text{camEye\_T\_camTarget} * \text{camTarget\_T\_localizer} * \text{localizer\_T\_calTarget} * \text{calTarget\_T\_calCoordSys} * \text{calCoordSys\_T\_focalRefFrame},$$

where calTarget_T_calCoordSys can allow for a transformation between the navigated target of the calibration object and an arbitrary coordinate system, and calCoordSys_T_focalRefFrame can allow for a transformation between that coordinate system and the focal reference frame. Both of these matrices may be identity matrices by design. The equation can thus be simplified as:

$$camEye\_T\_focalRefFrame = camEye\_T\_camTarget * camTarget\ T\ localizer * localizer\_T\_focalRefFrame.$$

XII. Robot Alignment of the Microscope Optical Axis to a Given Vector

In some embodiments, the digital surgical microscope head 110 can be mounted on a robotic arm 120. The robotic arm 120 may be controlled by a robot control module 820 in the microscope processing unit 420. The physical characteristics of the robot joints required to calculate robot end effector pose relative to the robot base (such as joint angles) may be known for all or most robot joints by design and/or calibration and/or real-time measurement during runtime. The further physical properties for calculating robot end effector pose relative to the robot base (such as nominal length and flexure under load and under pose change of the links connecting the joints) may be known by design and/or by calibration and/or by real-time measurement. Thus, the pose of the robot end effector (the most distal active joint or link of the robot itself) may be known relative to the robot base continually in real time and may be denoted as:

robotBase_T_robotEEff

The physical properties of all extensions such as coupler 140 and force-torque sensor 150 are also known by design and/or calibration, and/or measurement such that the pose of the distal end "control point" of e.g. 150 is known relative to the robot end effector and is denoted by:

EEff_T_controlPt

Further, the pose of the representative navigated target 210 on the digital surgical microscope head is known by design and/or measurement relative to a mounting datum 152 on the reference frame of which mounting datum is designed to mate coincidentally with the reference frame of the most distal reference frame such as 150 on the robot assembly before the camera head. Further improvements to the knowledge of said pose may be optionally made by measurement.

Thus the pose of the representative navigated target 210 on the digital surgical microscope relative to the control point 150 may be known and may be denoted by:

controlPt_T camTarget

With these and prior transformations previous described, the pose of each respective camera eye relative to the robot base may be calculated as follows:

$$robotBase\_T\_camEye = robotBase\_T\_robotEEff * robotEEff\_T\_controlPoint * controlPt\_T\ camTarget * camTarget\_T\_camEye$$

The robotEEff_T_camEye relationship may be sometimes referred to as the "hand-eye" pose relationship. Also or alternatively this hand-eye pose relationship can be discovered using known calibration techniques such as OpenCV's cv::calibrateHandEye method, and the math above may be reworked as:

$$robotBase\_T\_camEye = robotBase\_T\_robotEEff * robotEEff\_T\_camEye$$

The pose of the focal reference frame relative to the robot base is found using the previously described camEye_T_focalRefFrame function:

$$robotBase\_T\_focalRefFrame = robotBase\_T\_camEye * camEye\_T\_focalRefFrame \qquad \text{Eq 8}$$

The pose of the robot base in localizer space

The pose of the robot base m localizer space can be found using the following function:

$$Localizer\_T\_robotBase = localizer\_T\_camTarget * camTarget\_T\_controlPoint * controlPoint\_T\_robotEEff * robotEEff\_T\_\ robotBase$$

During planning phase 1060, useful features may be added to the patient data space to aid the surgeon in the execution of the surgical procedure. These features include but are not limited to surgical opening "cut by numbers" patterns, approach vectors (e.g., trajectory plans), and approach waypoints at which the digital surgical microscope can be posed repeatably to establish and evaluate progress.

A surgical opening in cranial surgery may be referred to as a craniotomy. During planning phase 1060 the user optionally can specify the outline of the desired opening. Critically, in traditional surgery such an approach is specified on the live user's skin using a surgical marking pen and is thus destroyed when the first layer of skin is removed (which is among the first steps in the procedure.)

The presently described integrated system enables the user to virtually draw such an opening plan in the patient data. This opening plan can then be displayed under user control for the entirety of the opening phase, e.g., beyond skin removal. Furthermore, the opening plan can address the three-dimensional nature of opening a patient. For example, instead of a simple line drawing, the plan can be multi-layer and/or three-dimensional to show the surgeon how to cut into the three-dimensional surface.

Figure 8:
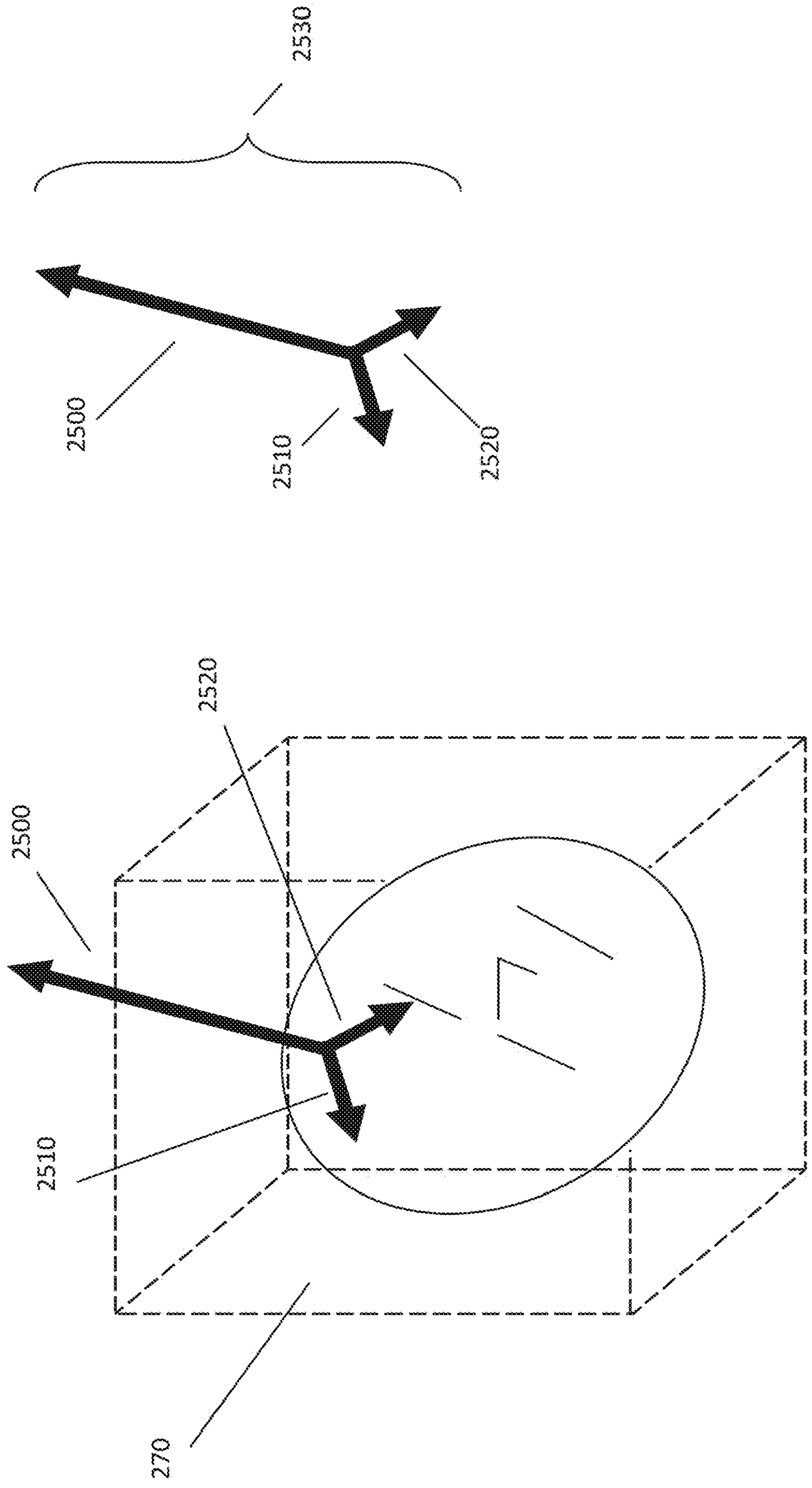
FIG. 8 is a diagram showing an example trajectory plan applicable to the integrated surgical navigation and visualization system, according to an example embodiment of the present disclosure.

FIG. 8 is a diagram showing an example trajectory plan applicable to the integrated surgical navigation and visualization system, according to an example embodiment of the present disclosure. A trajectory plan can be optionally added in the patient data space 270. The trajectory may comprise a path in patient data space along which the user desires the procedure to proceed. For example, a cranial neurosurgeon might plan a trajectory toward an aneurysm that avoids critical parts of the brain and favors more readily traversed regions. If the trajectory is complex, it may be split into separate smaller trajectories which are more readily represented and achieved (e.g., for piecewise linearly). Also or alternatively, waypoints may be added by the user in the patient data space showing desired camera poses relative to the patient. With the connection of robot space, camera space, and patient space allowed in systems and methods described herein, such waypoints can be visited at any time during the procedure. Furthermore, such opening, trajectory and waypoint planning can be updated and/or augmented at any time during the procedure.

An advantage of the presently described integrated system is that it provides the user the option to adjust visualization such that it is focused along the trajectory and optionally focused upon the "next step" in the trajectory. This adjusted visualization shows the surgeon the path where to proceed and indeed poses the microscope to be looking right at the place to do so. At least one example for providing this capability is described as follows.

The trajectory plan may be represented as a transformation in the patient data space:

$$\text{patientData\_}T\text{\_trajPlan} \quad (2.9)$$

The trajectory plan may primarily represent a vector 2500 along which the trajectory may proceed at the "next" step in the surgical procedure. It may be expedient (but optional) to represent the trajectory as a full reference frame such that an orientation about the primary vector 2500 is also specified. This orientation may be represented as two other axes 2510 and 2520. This enables the user to incorporate patient, surgeon and microscope positioning into the trajectory planning. Without such specification, the control algorithm merely needs to make a "best guess" at a sensible orientation for solved movements. For example, to ensure the correct orientation of the microscope head relative to the trajectory plan, a convention may be chosen such that a patient geometry keep-out is favored. Additional constraints may be added such as minimal movement, robot joint limits, and "outside looking in" orientation.

The preceding description may allow the robot control module 820 to pose the digital surgical microscope head such that it is looking along the trajectory planning path and further that it is focused on the "next step" of proceeding along that path. First the trajectory plan in the localizer space is determined as follows:

$$\text{localizer\_T\_trajPlan} = \text{localizer\_T\_patientTarget} * \text{patientTarget\_T\_patientData} * \text{patientData\_T\_trajPlan},$$

where each matrix on the right side are as described previously. Then the pose of the trajectory plan relative to the robot base can be found as:

$$\text{robotBase\_T\_trajPlan} = \text{robotBase\_T\_localizer} * \text{localizer\_T\_trajPlan}$$

Further, the trajectory plan can be replaced by other means of defining a pose in the patient data space, and the robot commanded to match or track said pose. Since various embodiments described herein provide connection of the camera space, the localizer space, and the robot space, such pose definition can be achievable by multiple means, including but not limited to: posing a navigated tool such as tool 252; the axis to which the alignment is performed can be defined arbitrarily within the navigated target space of such a tool; or the pose of a user's head, thereby enabling head tracking when a navigated target is connected directly or indirectly to the user's head for example to the 3D glasses 192. Such pose control of the camera can be relative to some starting position of the user's head (for example initialized upon some activation action such a pushbutton being pressed or a voice command saying, "Head tracking on".

Furthermore, the pose of a computer-vision trackable pattern mounted for example on a surgical tool may also be used to achieve pose definition. Similar to the head tracking just described, with some user activation function, the pose of the camera head is controlled by changing the pose of the trackable pattern, with the change in pose of the camera calculated from some starting pose measured at time of user activation. Depending on the activation function, this can provide hands-free control of microscope pose. Also, or alternatively, the pose of a navigation camera-trackable target mounted to a local part of the patient's anatomy such as a single vertebra during spine surgery. By tracking the movement of the vertebra the system provides a consistent view to the surgeon relative to the vertebra. This is especially useful when performing steps in the procedure that cause significant movement to the anatomy in question. For example as the vertebra moves, the camera pose may be updated to always be imaging the same place and in the same orientation where the surgeon is performing a laminectomy.

The pose of other navigated tools may also be used to achieve pose definition. For example, the camera may be posed continually to provide a clear view of the surgical site to the user showing for example the distal end of a primary tool and/or avoiding imaging the shafts of said tools which would normally block the visualization.

The focal reference frame may be matched to the trajectory plan reference frame. To drive the robot such that the optical axis of the digital surgical microscope is looking along the trajectory plan primary axis and optionally focused upon the trajectory plan origin, the pose of the trajectory plan in the space of the robot base can be set to be equal to the pose of the digital surgical microscope's focal reference space relative to the robot base as:

$$\text{robotBase\_T\_focalRefFrame} = \text{robotBase\_T\_trajPlan}$$

which is found in an alternative manner using:

$$\text{robotBase\_T\_trajPlan} = \text{robotBase\_T\_focalRefFrame} = \text{robotBase\_T\_robotEEff} * \text{robotEEff\_T\_controlPoint} * \text{controlPoint\_T\_camTarget} * \text{camTarget\_T\_camEye} * \text{camEye\_T\_focalRefFrame}$$

From the above equations, the robot pose robotBase_T_robotEEff may be required to match the trajectory plan is calculated using standard matrix math to isolate the robotBase_T_robotEEff function on the left hand side of the equation, as follows:

$$\text{robotBase\_T\_robotEEff} = \text{robotBase\_T\_trajPlan} * \text{trajPlan\_T\_camEye} * \text{camEye\_T\_camTarget} * \text{camTarget\_T\_controlPoint} * \text{controlPoint\_T\_robotEEff}$$

Further, since the focal reference frame is desired to be matched to the trajectory plan, e.g., robotBase_T_trajPlan=robotBase_T_focalRefFrame one gets:

$$\text{robotBase\_T\_robotEEff} = \text{robotBase\_T\_focalRefFrame} * \text{focalRefFrame\_T\_camEye} * \text{camEye\_T\_camTarget} * \text{camTarget\_T\_controlPoint} * \text{controlPoint\_T\_robotEEff}$$

The above recited equation can provide the pose of the robot to match the trajectory plan given the trajectory plan and the current poses of the digital surgical microscope and the patient reference frame.

An inverse kinematics routine is performed to determine a set of joint poses that satisfy the above equations and said set of joint poses may be sent to robot control module 820, which may then proceed in a stepwise manner toward said set of poses.

Since some parameters may change during the robot movement toward the desired set of poses required to move the focal reference frame toward being coincidental with the trajectory plan reference frame, a periodic update of the calculation of robotBase_T_robotEEff and its underlying enabling equations may be calculated and the movement "goal" of the robot control module.

Such update may provide, for example, a dynamic tracking of an arbitrary reference frame such as a navigation target attached to a surgical tool or other trackable tool. For example a spinal dilator such as Medtronic MetRx might have a navigated target mounted to it and the robot could track the center of the shaft of the MetRx toolset, thereby providing the microscope to continually image "down the tube" without any direct input needed from the user.

Since a trajectory is at its core a path, trajectory planning can represent many things such as: a desired surgical approach; a shunt installation path; a desired pedicle screw orientation, and/or an installation path for spine surgery.

The various embodiments described herein allow the trajectory to be drawn onscreen under user control, appearing due to the system's careful calibration processes in the correct location, orientation, size and perspective relative to the live surgical view.

For example, a trajectory can be corrected using this technology. The patient may be marked with real and virtual marks at the time of "best patient registration." Future movements of the patient relative to the patient navigation target (thereby degrading the registration accuracy) may be corrected by visually re-aligning the real and virtual marks. The correction thus applied can also be applied to the trajectory plan(s), thereby correcting said plan(s).

A trajectory can also be corrected using this technology, for example, when the patient's brain shifts due to pressure changes and gravity. A correction may be applied to the plan either manually by the user or under an automated brainshift correction algorithm. The correction can then be used by the system as described for trajectory plans in general.

It will be appreciated that all of the disclosed methods and procedures described herein can be implemented using one or more computer programs or components. These components may be provided as a series of computer instructions on any conventional computer readable medium or machine-readable medium, including volatile or non-volatile memory, such as RAM, ROM, flash memory, magnetic or optical disks, optical memory, or other storage media. The instructions may be provided as software or firmware, and/or may be implemented in whole or in part in hardware components such as ASICs, FPGAs, DSPs or any other similar devices. The instructions may be configured to be executed by one or more processors, which when executing the series of computer instructions, performs or facilitates the performance of all or part of the disclosed methods and procedures.

It should be understood that various changes and modifications to the example embodiments described herein will be apparent to those skilled in the art. Such changes and modifications can be made without departing from the spirit and scope of the present subject matter and without diminishing its intended advantages. It is therefore intended that such changes and modifications be covered by the appended claims.

What is claimed is:

1. An integrated surgical navigation and visualization system comprising:

a single cart providing mobility;

a stereoscopic digital surgical microscope comprising a surgical visualization camera and a localizer;

one or more computing devices configured to house and jointly execute a surgical navigation module and a surgical visualization module, wherein the localizer is associated with the surgical navigation module, wherein the surgical visualization camera is associated with the surgical visualization module, and wherein the one or more computing devices are powered by a single power connection, thus reducing an operating room footprint;

a single unified display;

a processor; and memory storing computer-executable instructions which, when executed by the processor, cause the integrated surgical navigation and visualization system to:

generate a transformation of patient data associated with a patient to the surgical visualization camera;

calibrate the surgical visualization camera and the localizer;

provide visualization of a surgical site via the single unified display; and provide navigation of the surgical site responsive to user input.

2. The integrated surgical navigation and visualization system of claim 1, wherein the computer-executable instructions which, when executed by the processor, cause the integrated surgical navigation and visualization system to generate the transformation of patient data associated with the patient to the surgical visualization camera by:

generating, at a single zoom and a working distance for each camera eye associated with each of the surgical visualization camera and the localizer, a first transformation of the localizer to the surgical visualization camera, wherein the respective camera eye is configured to view a target position of the patient during runtime use of the integrated surgical navigation and visualization system; and generating, over a range of a zoom and the working distance for each camera eye associated with each of the surgical visualization camera and the localizer, a second transformation of the localizer to the surgical visualization camera, wherein the respective camera eye is configured to view the target position of the patient during the runtime use.

3. The integrated surgical navigation and visualization system of claim 2, wherein the computer-executable instructions which, when executed by the processor, further cause the integrated surgical navigation and visualization system to:

perform, using the first transformation of the localizer to the surgical visualization camera and the second transformation of the localizer to the surgical visualization camera, a patient registration of the patient to determine a pose of a relevant patient anatomy of the patient relative to the target position of the patient.

4. The integrated surgical navigation and visualization system of claim 3, wherein the patient registration comprises a transformation of the patient data associated with the patient to the target position of the patient.

5. The integrated surgical navigation and visualization system of claim 4, wherein the computer-executable instructions which, when executed by the processor, further cause the integrated surgical navigation and visualization system to:

generate, using the transformation of the patient data to the target position of the patient, a transformation of the target position of the patient to the localizer; and generate, based on the transformation of the target position to the localizer, a transformation of the patient data associated with the patient to the surgical visualization camera.

6. The integrated surgical navigation and visualization system of claim 3, wherein the computer-executable instructions which, when executed by the processor, further cause the integrated surgical navigation and visualization system to:

prompt a user to cause the patient registration of the patient using a focal point of the stereoscopic digital surgical microscope; and receive user input associated with the use of the focal point of the stereoscopic digital surgical microscope to cause the patient registration of the patient, wherein the user input is touchless.

7. The integrated surgical navigation and visualization system of claim 6, wherein the computer-executable instructions which, when executed by the processor, further cause the integrated surgical navigation and visualization system to receive the user input associated with the use of the focal point via photogrammetry or stereogrammetry.

8. The integrated surgical navigation and visualization system of claim 1, wherein joint execution of the surgical navigation module and the surgical visualization module is configured to reduce communication latency and connectivity risk.

9. The integrated surgical navigation and visualization system of claim 1, wherein the computer-executable instructions which, when executed by the processor, further cause the integrated surgical navigation and visualization system to:

synchronize, in real time, the visualization of the surgical site with the navigation of the surgical site by providing integrated navigation information and microscope surgical site visualization via the single unified display.

10. The integrated surgical navigation and visualization system of claim 1, wherein the computer-executable instructions which, when executed by the processor, further cause the integrated surgical navigation and visualization system to:

provide navigation information overlaying the visualization of the surgical site at a same plane of focus for all views.

11. The integrated surgical navigation and visualization system of claim 1, wherein the computer-executable instructions which, when executed by the processor, further cause the integrated surgical navigation and visualization system to:

control a position of the stereoscopic digital surgical microscope with a given reference.

12. The integrated surgical navigation and visualization system of claim 11, wherein the computer-executable instructions which, when executed by the processor, further cause the integrated surgical navigation and visualization system to control the position of the stereoscopic digital surgical microscope by:

receiving a user input associated with a pre-planned trajectory for the navigation of the surgical site; and aligning the given reference of the stereoscopic digital surgical microscope with the pre-planned trajectory.

13. The integrated surgical navigation and visualization system of claim 11, wherein the given reference of the stereoscopic digital surgical microscope aligns quasi-continuously in quasi-real-time with a central axis of a surgical port or a spinal dilator tool.

14. The integrated surgical navigation and visualization system of claim 1, further comprising:

an orientation adjustment handle; and a navigation target illumination device in the localizer.

15. A method for integrating surgical navigation and surgical visualization in a computing system having one or more processors, the method comprising:

performing a startup of the computing system, causing a startup of a surgical navigation module and a surgical visualization module, wherein the surgical navigation module and the surgical visualization module are jointly housed in and executed by the computing system;

generating a transformation of patient data associated with a patient at a surgical site to a surgical visualization camera associated with the surgical visualization module;

calibrating the surgical visualization camera and a localizer associated with the surgical navigation module;

providing navigation of the surgical site responsive to user input; and providing visualization of the surgical site via a single unified display.

16. The method of claim 15, wherein generating the transformation of the patient data to the surgical visualization camera comprises:

generating, at a single zoom and a working distance for each camera eye associated with each of the surgical visualization camera and the localizer, a first transformation of the localizer to the surgical visualization camera, wherein the respective camera eye is is configured to view a target position of the patient during runtime use of the computing system; and generating, over a range of a zoom and the working distance for each camera eye associated with each of the surgical visualization camera and the localizer, a second transformation of the localizer to the surgical visualization camera, wherein the respective camera eye is is configured to view the target position of the patient during the runtime use.

17. The method of claim 16, wherein generating the transformation of the patient data to the surgical visualization camera further comprises:

performing, using the first transformation of the localizer to the surgical visualization camera and the second transformation of the localizer to the surgical visualization camera, a patient registration of the patient to determine a pose of a relevant patient anatomy of the patient relative to the target position of the patient, the patient registration comprising a transformation of the patient data associated with the patient to the target position of the patient;

generating, using the transformation of the patient data to the target position of the patient, a transformation of the target position of the patient to the localizer; and generating, based on the transformation of the target position to the localizer, a transformation of the patient data associated with the patient to the surgical visualization camera.

18. The method of claim 15, further comprising:

controlling a position of a stereoscopic digital surgical microscope with a given reference by:

receiving, by the computing system, a user input associated with a pre-planned trajectory for the navigation of a surgical site by the stereoscopic digital surgical microscope; and aligning the given reference of the stereoscopic digital surgical microscope with the pre-planned trajectory.

19. A non-transitory computer readable medium for use on a computing device containing computer-executable programming instructions for integrating surgical navigation and surgical visualization, the computer-executable programming instructions comprising:

performing a startup of the computing device, causing a startup of a surgical navigation module and a surgical visualization module, wherein the surgical navigation module and the surgical visualization module are jointly housed in and executed by the computing device;

generating a transformation of patient data associated with a patient at a surgical site to a surgical visualization camera associated with the surgical visualization module;

calibrating the surgical visualization camera and a localizer associated with the surgical navigation module;

providing navigation of the surgical site responsive to user input; and providing visualization of the surgical site via a single unified display.

20. The non-transitory computer readable medium of claim 19, wherein generating the transformation of the patient data to the surgical visualization camera comprises:

generating, at a single zoom and a working distance for each camera eye associated with each of the surgical visualization camera and the localizer, a first transformation of the localizer to the surgical visualization camera, wherein the respective camera eye is configured to view a target position of the patient during runtime use of the computer device;

generating, over a range of a zoom and the working distance for each camera eye associated with each of the surgical visualization camera and the localizer, a second transformation of the localizer to the surgical visualization camera, wherein the respective camera eye is configured to view the target position of the patient during the runtime use;

performing, using the first transformation of the localizer to the surgical visualization camera and the second transformation of the localizer to the surgical visualization camera, a patient registration of the patient to determine a pose of a relevant patient anatomy of the patient relative to the target position of the patient, the patient registration comprising a transformation of the patient data associated with the patient to the target position of the patient;

generating, using the transformation of the patient data to the target position of the patient, a transformation of the target position of the patient to the localizer; and generating, based on the transformation of the target position to the localizer, a transformation of the patient data associated with the patient to the surgical visualization camera.

* * * * *